United States Patent [19]
Cohen et al.

[11] Patent Number: 4,776,345
[45] Date of Patent: Oct. 11, 1988

[54] INTERACTIVE DETERMINATION OF SLEEP STAGES

[75] Inventors: Daniel E. Cohen, Eden Prairie; Milton W. Anderson, Eagan; Rihab Fitzgerald, Minneapolis, all of Minn.

[73] Assignee: CNS, Inc., Eden Prairie, Minn.

[21] Appl. No.: 93,576

[22] Filed: Sep. 4, 1987

[51] Int. Cl.$^4$ .............................................. A61B 5/04
[52] U.S. Cl. ..................................................... 128/731
[58] Field of Search ............................... 128/731–733; 364/415, 417

[56] References Cited

U.S. PATENT DOCUMENTS

| | | |
|---|---|---|
| 3,548,812 | 12/1970 | Frost ..................................... 128/731 |
| 4,579,125 | 4/1986 | Strohl et al. ........................ 128/731 |
| 4,610,259 | 9/1986 | Cohen et al. ....................... 128/731 |

OTHER PUBLICATIONS

Cox, J. R. et al., "Digital Analysis of the EEG, BP and ECG", Proc IEEE, vol. 60, No. 10, Oct. 1972, pp. 1137–1164.
Courtney, P. et al., "A Hybrid Computer System for Unsupervised Storing of Sleep Records", Conf. Proc. of 9th Ann. Rcky Mtn Bioengrg Symposium, vol. 9, Omaha, Neb. (1–3 May 1972), pp. 161–167.
Wallingford, E. E. et al., "A Dynamic EEG Frequency Analyzer", IEEE Trans. on Instr. and Meas., vol. IM-27, No. 1, Mar. 1978, pp. 70–73.

Primary Examiner—Francis J. Jaworski
Attorney, Agent, or Firm—Kinney & Lange

[57] ABSTRACT

Such representations may include the average frequency value of electroencephalographic signals, the logarithm of the power of electromyographic signals, and eye movement indications from electrooculographic signals. Criteria for dividing the records of such representations in the system into stages of sleep can be set by a system operator reviewing these records based on accepted stage definition rules. In addition, transient events such as sleep spindles, etc., in these records can be selected therefrom by criteria set by the system operator also based on accepted rules therefor.

41 Claims, 12 Drawing Sheets

INTERACTIVE DETERMINATION OF SLEEP STAGES

BACKGROUND OF THE INVENTION

The present invention relates to determination of waking and sleep stages experienced by a resting subject from whom various physiological data are obtained and, more particularly, determining, through an operator viewing a display of representations of such data as a basis for setting criteria, waking and different stages of sleep.

Substantial research has been undertaken directed toward understanding the nature of sleep and sleep disorders. This research has yielded considerable information concerning human patterns of sleeping and not sleeping, the physiological activities occurring in humans during sleep including sleep structure as to type, and various cognitive aspects of sleeping, such as dreaming. In addition, substantial information has been obtained concerning various sleep disorders.

In assessing the physiological activity occuring during sleep, various kinds of signal data are obtained, recorded and analysed. A primary signal which is obtained yields the electroencephalographic signal data which is used as a reference with respect to which sleep events and other signals obtained are correlated. The other kinds of signals which are almost always obtained in sleep research, or in clinical evaluations, are electromyographic signals and electrooculographic signals. In addition, other often obtained signals are electrocardiac signals, respiration signals, blood oxygen saturation signals, and the like.

In reviewing and evaluating the data obtained from such signals, researchers have come to the conclusion that sleep is structured in five different characteristic patterns or stages when viewed against the electroencephalographic signal data for normal adults. This has led to a set of rules or descriptions which have become generally accepted as a basis for classifying a physiological signal data record of a sleeping adult into the various characteristic kinds of sleep which have occurred, i.e., "scoring" waking and sleep stages in the physiological signal record.

Though the rules have relatively detailed descriptions of the various sleep stages, the following gives a rather general summary of the stages under the rules of descriptions. The recorded data is viewed as a succession of "epochs," each of which is a data accumulation period of typically 30 seconds, though other periods such as 20 seconds and 60 seconds can also be used. Each such epoch is then scored as being in the waking stage or one of the sleep stages. Frequency ranges in the electroencephalographic signals are classified into the four traditional frequency ranges for such signals, these being the "delta" range of from 0.5 to 2.0 Hz, the "theta" range of from 2.5 to 7.5 Hz, the "alpha" range of from 8.0 to 12.5 Hz, and the "beta" range of 13.0 Hz or greater.

The waking stage and sleep stage descriptions in terms of the physiological signals obtained are then as follows:

Stage W: The waking stage has electroencephalographic signals with frequency content in the alpha range or low voltage, mixed frequency range result, or both. This stage is usually accompanied by a relatively high electromyographic signal level and by rapid eye movements.

Stage 1: This stage has relatively low voltage, mixed frequency electroencephalographic signals, most of which are in the theta frequency range. There is an absence of sleep spindles and K-complexes (both described below). This is also true of rapid eye movements (described below). The electromyographic signal data amplitudes are usually greater than those in Stage REM as indicated below. Epochs between two sleep spindles which are more than three minutes apart and which meet the criteria otherwise for Stage 1 are considered to be Stage 1 epochs, as are those epochs following a movement arousal (described below) between pairs of sleep spindles separated in time by less than three minutes.

Stage 2: The electroencephalographic signal must have sleep spindles or K-complexes, or both, in an epoch but not have a predominance of high amplitude waveform portions with frequency content in the delta frequency range. The electromyographic signal usually has amplitudes above those used in describing Stage REM. If sleep spindles or K-complexes are not present in the epoch, the epoch must be between a pair of sleep spindles or K-complexes not separated in time by more than three minutes, and without any intervening movement arousals or, in an exception for the occurrence of EMG amplitudes consistent with Stage REM, there must be no intervening rapid eye movements. If the sleep spindles or K-complexes are separated by more than three minutes, score the epoch as Stage 1. Occurrence of a movement arousal between pairs of sleep spindles or K-complexes separated by less than three minutes leads to a determination on the basis of the epochs, prior to the movement arousal, being scored Stage 2 epochs while those after the arousal are scored Stage 1 epochs.

Stage 3: The electroencephalographic signal data must have 20%, but not more than 50%, of the epoch having waves in the delta frequency range with amplitudes greater than 75 U V peak-to-peak for that epoch to be considered sleep at this stage. The occurrence or not of sleep spindles or K-complexes has no effect on the determination that sleep is of this stage.

Stage 4: The electroencephalographic signal data in an epoch must have a frequency content in the delta range with an amplitude greater than 75 U V peak-to-peak during 50% or more of that epoch for it to be considered sleep of this stage. Again, the occurrence of sleep spindles or K-complexes has no effect on the determination of sleep in this stage.

Stage REM: The electroencephalographic signal in the epoch is of a relatively low voltage, mixed frequency coupled with rapid eye movements occurring in the vicinity of the epoch and associated with a relatively low electromyographic signal level. An epoch cannot be considered as part of this stage of sleep if more than one-half thereof occurs between two sleep spindles or K-complexes separated by less than three minutes with no intervening rapid eye movements. An epoch cannot be considered part of this stage of sleep either if the last significant movement arousal occurred more recently than the last rapid eye movement.

Sleep spindles, K-complexes, rapid eye movements and movement arousals are transient events, being of a short duration, which occur from time to time during gathering data from physiological signals measured on a subject. A sleep spindle is defined as an electroencephalographic signal waveform event of amplitude changes occurring in the 12.0 to 14.0 Hz range (considered by many to extend to the 11.0 to 15.0 Hz range) of a sufficient peak-to-peak amplitude with the rest of the waveform thereabout of a sufficiently lower frequency content with a time duration exceeding 0.5 seconds. A K-complex is a waveform portion having a negative peak preceding a positive peak with a time duration of these waveform events exceeding 0.5 seconds, with these peaks separated by a sufficient peak-to-peak voltage.

The electrooculographic signals obtained are taken from an electrode provided for each eye. One electrode is located approximately 1.0 cm. above and slightly lateral to the outer canthus of one eye, and the other electrode is located approximately 1.0 cm. below and slightly lateral to the outer canthus of the other eye, both referred to a common ear or mastoid electrode. Because eye movements in Stage REM and waking are binocularly synchronous, this arrangement provides opposite amplitude direction signals from these electrodes for almost all eye movements. Those signals that move together mostly represent electroencephalographic artifact, i.e., electrooculographic signal noise. The difference in the electrooculographic signals at points of sufficient amplitude indicates that a rapid eye movement or REM has occurred.

Movement arousals are found by noting occurrences of a sufficient change in the electromyographic signal data. A movement arousal occurs when such a change happens in conjunction with changes in either the electroencephalographic signal data or the electrooculographic signal data.

Even though the foregoing rules are offered in a summary description (the actual descriptions would require several pages), these descriptions suggest how much must be considered for each epoch being scored by a trained scorer. Since the typical adult night's sleep is seven or eight hours, epochs of 30 seconds duration will lead to a rather large number of epoch records to be considered by such a scorer in allocating the sleep of an adult to the various waking and sleep stages. Thus, a means for easing the tedious effort required of such a scorer would be desirable to reduce the time until the information contained in the acquired data becomes available, to reduce errors in the analysis of the data and to reduce cost.

SUMMARY OF THE INVENTION

The present invention provides a method for obtaining electroencephalographic and electromyographic signal data from a resting subject, providing a frequency content representation of said electroencephalographic signal and providing a signal strength representation of said electromyographic signal, providing frequency and signal strength values for allocating portions of at least a corresponding one of said representations, and based on said electroencephalographic and electromyographic signal data, and on such frequency and signal strength values, determining whether waking or which of the types of sleep have been experienced by the subject during the obtaining of the data. The frequency and signal strength values are provided based on estimating them along the corresponding one of the electroencephalographic frequency content representation and the electromyographic signal strength representation, reviewing representations of corresponding portions of the electroencephalographic signal data and the electromyographic signal data, respectively, and then entering them as the frequency and signal strength values if they are consistent with the stage of sleep under consideration. Electrooculographic data is also obtained for use in such stage determinations and for use in providing rapid eye movement counts.

DETAILED DESCRIPTION OF THE PREFERRED EMBODIMENTS

Electroencephalographic signals, electromyographic signals and electrooculographic signals are analog signals obtained from a subject which must be sampled in amplitude over a selected interval of time with each such sample converted to its digital equivalent value if such signals are to be treated by a digital computer. Although treating these signals somewhat further, or completely, by analog signal processing means is possible, such methods are not nearly as convenient as digital methods, nor as accurate. These consecutive digitized samples, consecutive in the time order in which they are obtained from the sampled signal, can have the frequency content or the power content thereof assessed most conveniently if they are transformed from the time domain to the frequency domain by some fast Fourier transform (FFT) algorithm. The results of the transformation represent a frequency spectrum from which the power spectrum can be obtained in a well known manner.

Figure 1C:
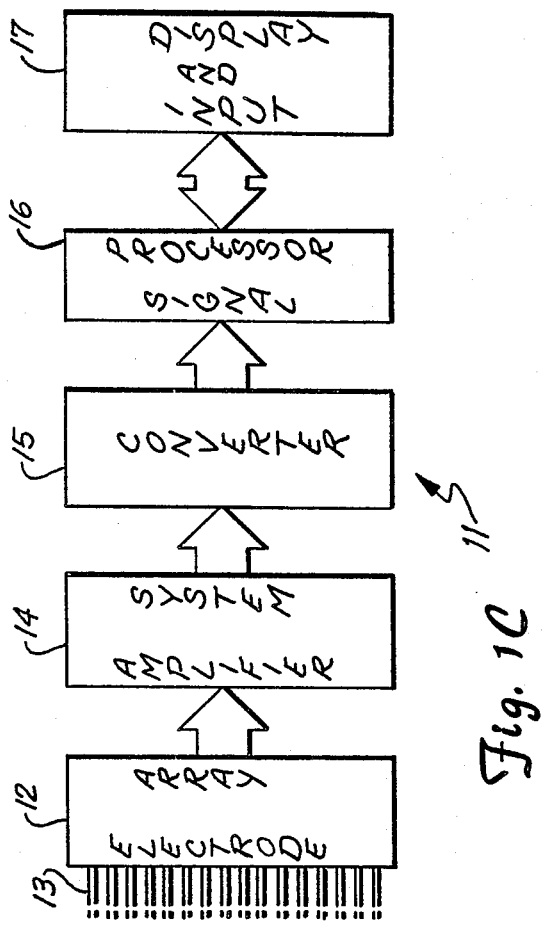
FIGS. 1A, 1B and 1C show a block diagram of the present invention and two views of a subject's head with markings.
Figure 1A:
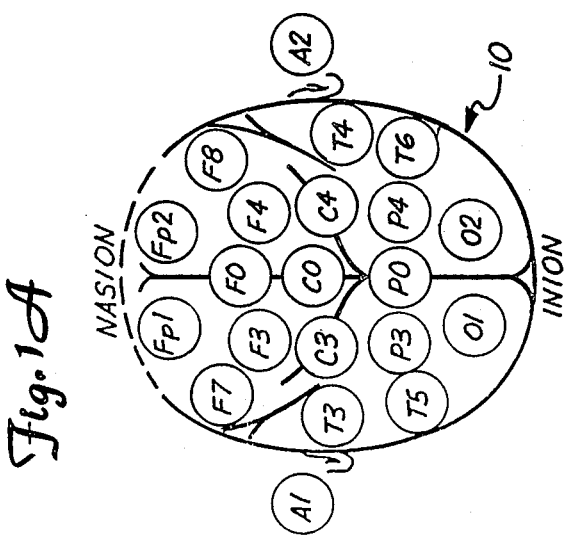

FIG. 1A shows the top of a subject's or patient's head, 10, and the standard positions on the scalp thereof for locating electrodes for electoencephalographic monitoring. The locations for the electrodes are identified by the commonly used designations FP1, FP2, FO, F3, F4, F7, F8, T3, T4, T5, T6, C0, C3, C4, P0, P3, P4, O1 and O2. There are also shown reference electrode locations A1 and A2 for the attachment of reference electrodes, these being commonly attached to one or both of the patient's ears. These standard positions can be, but need not be, used for present purposes. In fact, the signals for sleep monitoring are usually taken only at one of positions C3 or C4 with perhaps the other used as a redundant signal source to guard against any signal acquisition failure.

Figure 1B:
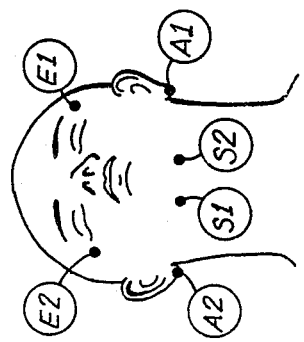

Also shown in FIG. 1B is the view of the underside of the head of subject 10 in an upward looking view of the face of subject 10. As described above, electrodes for electrooculographic signals are shown at position E1 located approximately 1 cm. above and slightly lateral to the outer canthus of the left eye. Another electrode is located approximately 1 cm. below and slightly lateral to the outer canthus of the right eye at position E2. Both of these electrodes can be referred to another location on the head of subject 10, either at ear A1 or in the nearby mastoid.

Finally, an electrode for obtaining an electromyographic signal is placed at one of the submental points beneath the chin S1 or S2. A reference electrode is placed at the other submental location (S2 if S1 is initially chosen) or can be placed directly on the chin.

To the right of the two views of head 10 in FIG. 1C is a sleep monitoring system, 11, for analyzing the electroencephalographic, electromyographic and electrooculographic signals obtained from the electrodes placed on subject 10 as just described. Analyzer system 11 has an electrode array module, 12, which has extending therefrom, though arbitrarily shortened in FIG. 1C to avoid obscurance, coupling cables, 13. Typically, there are sixteen electrodes for acquiring the signals already described plus other signals often used in sleep analysis, as indicated above. For those cables being used, the distal ends thereof are connected to the electrodes described above, including the reference electrodes connected as also described above, though other possibilities exist and can be used. The electrodes need not be shown in FIG. 1C because they are well known pieces of standard equipment available for use with electroencephalographic, electromyographic and electrooculographic testing. The electrodes not shown are intended to be placed at the designated locations on head 10 of the subject as described above.

The signals obtained by electrode array module 12 are transmitted to an amplifying system, 14, which contains one amplifier for each of cables 13. Typically, each of these amplifiers is a differential amplifier and measures the signal transmitted by its corresponding coupling cable 13 with respect to the further cables used as reference levels attached to head 10. These amplifiers provide a gain on the order of 70,000 and can amplify signals containing frequencies up to several tens of Hz without a degradation because of any frequency response limits of the amplifier. Such amplifiers need not be further described as they are well known for use in these arrangements. For sleep analysis, many of these amplifiers are not used and can be bypassed or set at a gain of one.

The amplified electroencephalographic, electromyographic and electrooculograhpic analog signals are provided from amplification module 14 (if used) to an analog multiplexer and then to an analog-to-digital converter both contained in a conversion module, 15. Consecutive samples, taken over a selected time interval, of the amplitude of each electrode acquired analog signal have digital values provided therefor in conversion module 15 in a well known manner. Conversion module 15 has been found to provide adequate resolution, for the present state of the art, if an analog sample is converted into a digital representation as a binary number of 12 magnitude bits and a sign bit.

As is well known, the taking of samples is repeated at fixed intervals at a rate or frequency which must exceed twice the highest frequency in that one of the electroencephalographic, electromyographic or electrooculographic signal which is to be represented by the samples if that signal is to be fully represented. Thus, if the upper frequency content of a signal is uncertain, sampling rates should be increased accordingly to the point where there is no longer any concern about having exceeded twice the highest rate signal. A way of assuring that the upper frequency is known for sampling purposes is to pass that signal through a filter. A typical sampling rate for module 15 in these circumstances would be 256 Hz, a rate adequate for the present state of the art if the electroencephalographic signal has passed though a low pass filter with a cutoff frequency set at 70 Hz with a 6 b per octave rolloff. Converters capable of the performance described in this paragraph are well known and readily available, and so require no further description here.

Digitized samples provided in conversion module 15 are provided to a signal processing means, 16. Digitized samples from each of the signals obtained from a location on head 10 are analyzed there in connection with various criteria from an operator to determine the waking and various stages of sleep indicated in the data obtained from head 10 of the subject in what is usually a test of several hours, typically an adult's full night of sleep of seven or eight hours.

A display and input module, 17, is in communication with signal processing means 16. An operator, in front of display and input module 17, can receive prompts and queries from signal analyzing system 16 on the display of module 17. Independently, or in response to such prompts and queries, the operator can, through the input portion of module 17, introduce information into module 17 for transmission to signal processing means 16. In addition, the results obtained by signal processing means 16, in analyzing the data obtained from the head of subject 10 as just described and in connection with the inputs from the operator at the input portion of module 17, can provide results which will then be presented on the display of module 17. Such a display module may include a video terminal, printer, or a keyboard, or any other convenient apparatus for use therein.

Figure 2:
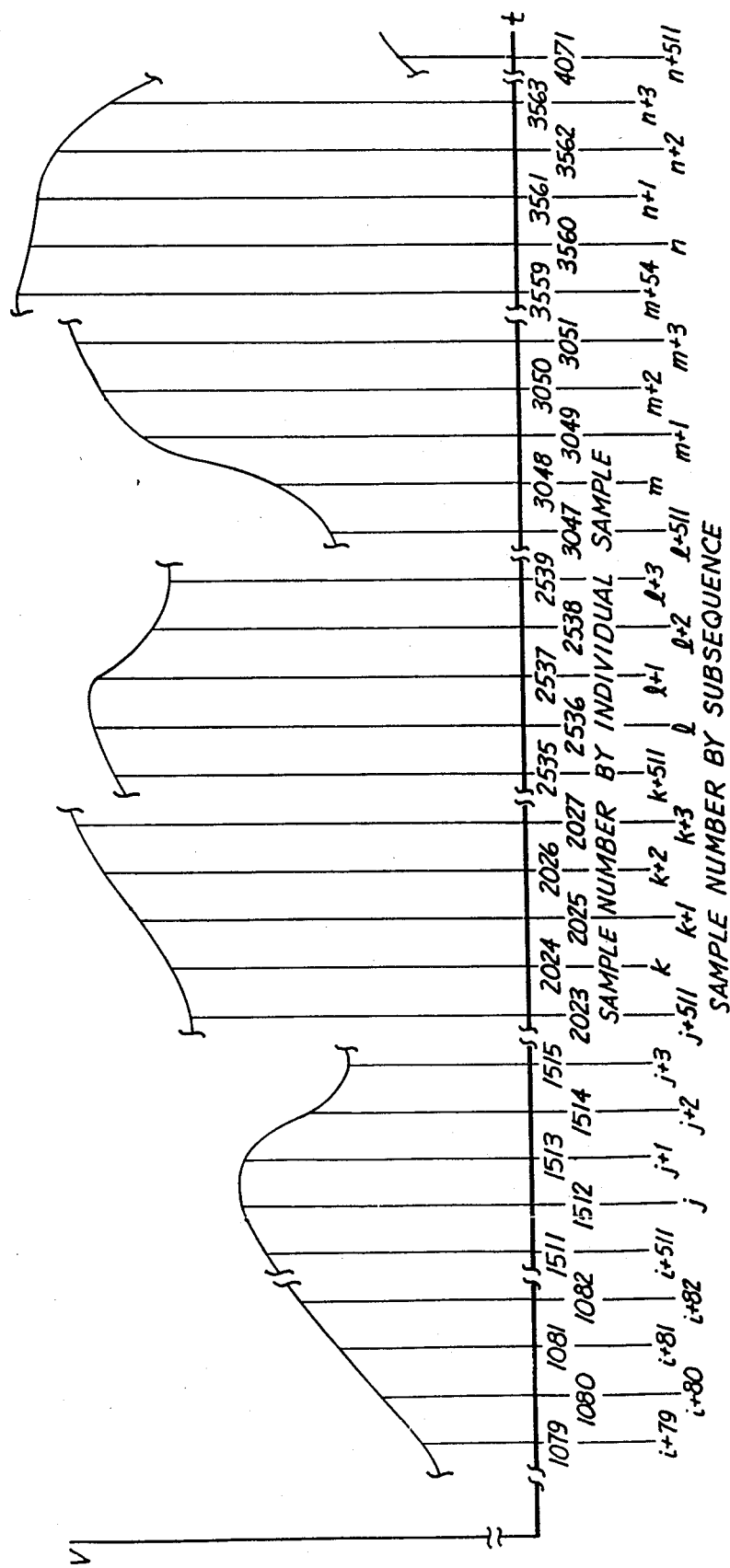
FIG. 2 shows a signal obtained in the system of FIG. 1, FIGS. 3A through 3F show displays provided by the system of FIG. 1C, FIGS. 4A through 4F show a flow chart followed in providing operator supplied criteria and in applying decision rules under the system of FIG. 1C.

A portion of a typical waveform which could represent an electroencephalographic, electromyographic or electrooculographic analog voltage signal that is transmitted by one of the coupling, or data gathering cables 13 is shown in FIG. 2. There the origin along the time axis has been set to zero at an arbitrary point. The measured electrical potential appearing in the signal is plotted on the vertical action as a voltage, v. Thin vertical lines intersecting the waveform are drawn from the waveform across the time axis down to a number which represents the number of the sample taken for that point of the waveform portion shown.

Note that breaks in both the time axis and the voltage axis are indicated near the origin so that this graph represents just a particular portion of the signal waveform chosen for illustration. That is, there is no significance in having chosen samples beginning with 1079 other than illustrating an arbitrary portion of a typical waveform. The entire waveform for each of cables 13 would be acquired over an interval of time typically measured, for example, in hours for an analysis of an adult's typical night of sleep of seven or eight hours. The actual digitized voltage values for the sample shown in FIG. 2 are not given, as these are unnecessary for purposes of explanation.

The consecutive samples ordered in time are numbered consecutively by the first numbering sequence in FIG. 2, this numbering of the samples from this signal being designated SAMPLE NUMBER BY INDIVIDUAL SAMPLE. The portion of the waveform shown begins with sample number 1079, goes to sample number 1082, where a break is shown along the time axis and in the waveform such that the next sample shown is sample number 1511. This pattern of breaks in the time axis, and correspondingly in the waveform, is continued along the time axis so that only portions of the waveform are shown while large portions of the waveform between samples 1079 and 4071 are omitted.

This breaking into portions of the waveform, and of corresponding portions of the time axis, was done to permit showing a renumbering of the samples on the basis of dividing them up into subsequences corresponding to segments of the waveform. That is, the sequence of individual samples is considered from the viewpoint of being a consecutive sequence of such subsequences which together provide the same sequence samples as the original sequence of samples taken of the example waveform. This second numbering of those same samples covered by the first numbering is designated in FIG. 2 as SAMPLE NUMBER BY SUBSEQUENCE.

This numbering by subsequence is shown with the $i^{th}$ subsequence arbitrarily beginning with that sample numbered 1000 from the first numbering which then serves as the zeroth sample of this $i^{th}$ subsequence. This $i^{th}$ subsequence continues through sample 1511 in the first numbering method which serves as a last sample in the $i^{th}$ subsequence, or sample number $i+511$ in the second numbering method. Immediately thereafter begins the $j^{th}$ subsequence with the zeroth sample in that subsequence designated j in the second numbering method and continuing through $j+511$. These second numbering method numbers in the $j^{th}$ subsequence correspond to samples number 1512 through 2023 in the first numbering method. This sort of relationship between the first and second numbering methods continues in the other portions of the example waveforms shown in FIG. 2, continuing through the $k^{th}$, $l^{th}$, $m^{th}$ and $n^{th}$ subsequences.

Thus, the sequence of samples of the example waveform portion shown in FIG. 2 can be considered as either a set of consecutive individual samples ordered in time, or a set of consecutive subsequences ordered in time with the consecutive samples in each subsequence also ordered in time. In effect, each subsequence covers a selected duration of time along the time axis in FIG. 2, the duration shown in this example set by each subsequence containing 512 individual samples of a waveform segment. The sequence of subsequences of samples of the example voltage signal shown, whether electroencephalographic, electromyographic or electrooculographic, can be represented as a $v_j(t_i)$, where j is an integer representing the number of a subsequence and i is an integer representing the number of time sample point within a subsequence and which can range from 0 to 511. Thus, a subsequence lasts two seconds at the chosen sampling rate of 256 samples per second. There need be no particular limit over which j can range. Hence, conversion module 15 presents each $v_j(t_i)$ as a subsequence of samples for each one of the electroencephalographic, electromyographic or electrooculographic signals to signal processing module 16.

Signal processing module 16 receives consecutive $v_j(t_i)$ for each electroencephalographic signal, electromyographic signal and electrooculographic signal, and provides an estimate of either the amplitude spectrum or the power spectrum, or both, for that set of samples contained in each subsequence for each signal. Thus, there is a succession of amplitude spectra or power spectra, or both, formed for each signal, one such spectrum formed for each consecutive subsequence of samples provided for that signal, leading to a plurality of amplitude or power spectra successions when considering all of the signals. (Some subsequences may not have spectra formed therefor or, if formed, not further used in the system if they are found too badly contaminated with signal artifacts or noise.) Also, the sequence of samples may be used directly without transformation to the frequency domain for some of the analysis if measurements in the time domain are necessary for that portion of the analysis.

Such amplitude or power spectra are established, as indicated, by use of transform techniques selected from many well-known techniques to transform the signals from the time domain to the frequency domain such as the fast Fourier transform technique. Power spectra of such transformed signals can then be estimated by a selected one of well-known techniques and can be represented as $V^2(f_k)$ where k is an integer which is a number of frequency point for which a value is presented in a spectrum. One representation that has been found sufficient for the electroencephalographic signal is provided by having a frequency component at every half Hertz through 30 Hz so that k ranges from 1 through 60. Other frequency range choices can be made.

A succession of power spectra are found, for instance, with there being one power spectrum found for each subsequence of the electroencephalographic signal obtained from position C3 or C4 on head 10 of the subject. This succession of electroencephalographic power spectra is used to provide a representation of the frequency content of the electroencephalographic signal in each epoch, and so forms a basis for an operator at display and input module 17 for entering criteria to be met by the electroencephalographic signal in determining waking or the stages of sleep for each epoch, as will be described below. The frequency content representation chosen is the average frequency value in an epoch as opposed to the traditional delta, theta, alpha and beta frequency ranges indicated above. Since the stage rules or descriptions, as described above, were presented somewhat tied to these traditional frequency range concepts, a modification of these rules is used in connection with the analyses performed by system 11, as will be described below.

In obtaining an epoch average frequency value, there is first found an average frequency value for each spectrum in the succession thereof based on the electroencephalographic signal. This spectrum average frequency is the weighted average of the frequencies present in the frequency range from 0.5 Hz to 30 Hz, to keep the frequency range in the representation example indicated above, as weighted by the power values occurring therein. This average frequency value $AFV_s$ for each subsequence spectrum can be found from the following:

$$AFV_{s-p} = \frac{\sum_{k=1}^{n} V^2(f_k)f_k}{\sum_{k=1}^{n} V^2(f_k)}$$

The p indicates which subsequence in an epoch is indicated. As the power spectra representation example description above suggests, the value of n in this equation to be in accord with that representation choice is 60. These average frequency values $AFV_{s-p}$ for each subsequence in an epoch can then be combined in an arithmetic average to determine the average frequency value for the epoch as follows:

$$AFV_e = \frac{\sum\limits_{p=1}^{m} AFV_{s-p}}{m}.$$

Choosing an epoch of typical duration, which would be 30 seconds as previously indicated, leads to m in this equation having a value of 15. This epoch average frequency $AFV_e$ represents the frequency content of the electroencephalographic signal in an epoch as a single value waveform, giving consideration to the amplitudes reached at each frequency. This concept of amplitude weighted frequency avoids the necessity of determining the frequency content in each of the traditional delta, theta, alpha and beta frequency ranges, and hence is a much more convenient representation of the frequency content of the electroencephalographic signal.

The sequence of subsequences of the electroencephalographic signal can also be considered as a succession of amplitude spectra, with an amplitude spectrum formed for each subsequence therein, as a basis for detecting the presence of sleep spindles. A sleep spindle, as indicated above, is considered to be a burst of waveform amplitude changes with a frequency content of from 11 to 15 Hz, typically 12 to 14 Hz, of a sufficient amplitude and lasting for at least 0.5 seconds and occurring along an underlying waveform containing lower frequencies. Thus, each subsequence must be broken up into secondary sub-subsequences of 0.5 seconds duration and the spectra found for each such sub-subsequence to assure that the 0.5 second requirement of the 11 to 15 Hz activity criteria is considered.

Signal processing module 16 can determine for each spectrum corresponding to a sub-sequence, after applying a "windowing" function such as the $Cos^4$ function to reduce edge effects, the amplitudes of the frequency components at every half Hertz in the spectrum between 11 and 15 Hz which are summed. This sum is, in turn, divided by the sum of the amplitudes at every half Hertz contained within other sub-subsequence spectra thereabout from 0.5 to 20 Hz. If the resulting ratio is greater than a specified value which the operator at display and input module 17 can set, a sleep spindle is taken to have occurred during that sub-subsequence if the average frequency value $AFV_{s-p}$ for that subsequence is below a specified value which can also be set by the operator. This relating of significant frequencies to other frequencies must be done to avoid finding false sleep spindles because, for instance, during waking much of the electroencephalographic signal may have a frequency content between 11 and 15 Hz which would erroneously indicate the occurrence of a sleep spindle. The sleep spindles found to have occurred in any subsequence can be added together in number for all of the subsequences occurring in an epoch to thereby obtain the number of spindles occurring in that epoch.

The foregoing method of determining the occurrences of sleep spindles is closely aligned with the definition of sleep spindles. However, such a signal processing method for finding sleep spindles, in requiring so many findings of spectra and other determinations, can require that signal processing module 16 have a very fast computational capability or an auxiliary processing capability either of which may be quite expensive. As an alternative, signal processing module 16 can be used to determine the existence of sleep spindles using time domain methods. One such method is to effectively count the number of peaks occurring within a 0.5 second time duration to determine if the definition of a sleep spindle has been met.

The electroencephalographic signal subsequences in the time domain must be directly monitored by signal processing module 16 for the occurrence of K-complexes therein. A K-complex, as indicated above, has a sharp negative waveform portion in the electroencephalographic signal immediately followed by a positive waveform portion, having a sufficient magnitude between the peaks and which has the peaks separated in time by 0.094 to 0.250 seconds. Each subsequence is checked by signal processing module 16 for the occurrence of a negative peak followed immediately by a positive peak with the required minimum peak-to-peak amplitude difference and the required time difference between the occurrence of the negative peak and of the positive peak. The required K-complex peak-to-peak voltage minimum can be set by an operator in display and input module 17. In addition, the frequency content of the spectra associated with the subsequence involving the potential K-complex must fall within a selectable range, typically 3.0 to 7.0 Hz. By totaling the number of K-complexes which occur in subsequences occurring in an epoch, the total number of K-complexes for the epoch can be found.

A succession of power spectra can also be found for the electromyographic signal, there again being one spectrum found for each subsequence of samples taken of the electromyographic signal. From this succession of spectra, a succession of total powers in a selected frequency range, typically 18 to 34 Hz (done to eliminate lower frequency signal artifacts such as those due to movement), can be found through finding a total power in this frequency range for each spectrum in the succession. An arithmetic average of these total powers taken from each of the subsequences in an epoch provides an average total power in this frequency range of the electromyographic signal $EMG_e$ for that epoch. Because of the rather substantial variability of such total powers in the electromyographic signal, a logarithm of that value is usually presented for the epoch, this logarithm being taken with respect to the base 10, or $Log_{10} EMG_e$.

Other measures of signal strength, or amplitude excursion from a reference, rather than actual power computations can be used as indicators of electromyographic signal behavior. For instance, an average of the absolute values taken of the signal with respect to a suitable reference would provide a satisfactory measure of signal activity and serve as an indicator of signal power. An average of the signal amplitudes, such as found through integrating the signal, would be another indicator of signal strength.

The electromyographic signal sequence of subsequences of samples of the waveform in the frequency domain are monitored also to determine whether a significant change has occurred in the electromyographic signal as a basis for finding a movement arousal as indicated above. This is accomplished through finding the power of the electromyographic signal for each subsequence and dividing it by the average of powers of the electromyographic signal occurring in a selected number of preceding subsequences. If this ratio exceeds a specified value which can be set by the operator at display and input module 17, there is the possibility of a movement arousal having been noted. This is confirmed if a simultaneous change has occurred in either the electroencephalographic signal or the electrooculographic signal or both.

Such changes in these latter two signals are monitored by signal processing module 16 in a somewhat similar manner. The average frequency value occurring in each subsequence is found and is divided by the average of the average frequency values occurring in a selected number of preceding subsequences to see if the resulting ratio, or ratios, exceed corresponding specified values that can be set by the operator at module 17. A change in either of these latter signals simultaneous with the change in the electromyographic signal, either or both of which exceed the corresponding specified ratio values, provide a basis for concluding a movement arousal has occurred. Such movement arousals can be segregated on the basis of the size of the amplitude changes to being either ordinary movement arousals or large movement arousals. Totals of each, if desired, can be provided for each epoch.

As set out above, there are two different electrooculographic signals taken from head 10 of the subject. A succession of amplitude spectra is generated for each of these signals, there being one spectrum provided for each subsequence in the signal. A further composite signal is provided by subtracting one of the electrooculographic signals from the other to form a differential signal. Such a differential signal, as indicated, leads to cancelling out commonly occurring signal portions in each channel while providing a larger signal for those portions changing in opposite amplitude directions in each channel. The differential signal is formed as a sequence of samples with corresponding subsequences through the subtraction of the samples of one of the two electrooculographic signals from the sequence of samples of the other electrooculographic signal. A succession of amplitude spectra is then formed for the composite electrooculographic signal just as for the two individual electrooculographic signals.

With these three sample sequences available, rapid eye movements (REM's) can be detected from the electrooculographic signals. After thus finding the sequence of samples for the composite signal and its succession of spectra, signal processing module 16 determines for each spectrum in the succession thereof the total of the amplitudes of the frequency components occurring in a selected frequency range typically between 2 and 5 Hz. That total is divided by the average of the amplitude components between 2 and 5 Hz in the spectrum taken from the simultaneously acquired subsequences in each of the individual electrooculographic signals. If the resulting ratio is greater than a specified value which can be set by an operator at display and input module 17, then an eye movement is taken to have occurred. Keeping a count of the eye movements that have occurred in connection with each of the simultaneously acquired subsequences during an epoch permits providing a count of the total number of REM's which have occurred during that epoch.

The capability of signal processing module 16 to detect sleep spindles, K-complexes, movement arousals and rapid eye movements, along with the capability thereof for providing average frequency values for the electroencephalographic signal, and average total powers for the electromyographic signal, permits determining the waking and sleeping stages experienced by a resting subject during the gathering of data provided by the electroencephalographic, electromyographic and electrooculographic signals, if two further kinds of information are provided. A set of decision rules must be provided to signal processing module 16 to give a procedure for determining whether any given epoch is a waking epoch or an epoch to be allocated to one of the five sleep stages. In addition, the operator must provide various values, such as those required to be specified for determining the occurrence of the transient events of sleep spindles, K-complexes, REM's, and movement arousals. Beyond these values, the operator must provide some judgment values as to the electroencephalographic signal frequency content in portions of that signal that are consistent with waking and Stages 3 and 4 of sleep. The operator must also provide the judgment value as to which power levels of the electromyographic signal are consistent with REM sleep.

While specification parameters for the transient events can generally be provided that are satisfactory for a variety of subjects from which data are obtained, the latter two judgment values of frequency content and power content of the electroencephalographic and electromyographic signals, respectively, vary significantly from subject signal record to subject signal record. As a result, system 11 must provide an operator at display and input module 17 with the opportunity of judging the sleep record of each subject as a basis for providing those frequency and power values necessary for finding waking and the various stages of sleep.

FIGS. 3A through 3F show an example of a set of various displays which are made to appear on display module 17 for use in judging (i) which values are proper in determining which portions of the electroencephalographic signal have frequency content consistent with Stages 3 and 4 of sleep and waking, and (ii) which portions of the electromyographic signal have powers consistent with sleep in the REM stage. The information on the displays is provided by signal processing module 16 to display and input module 17. The displays prompt the operator for input values which are then supplied to signal processing means 16 by display and input module 17. Such values are kept in memory portions of signal processing module 16, as are the transient event specified parameters.

Figure 3A:
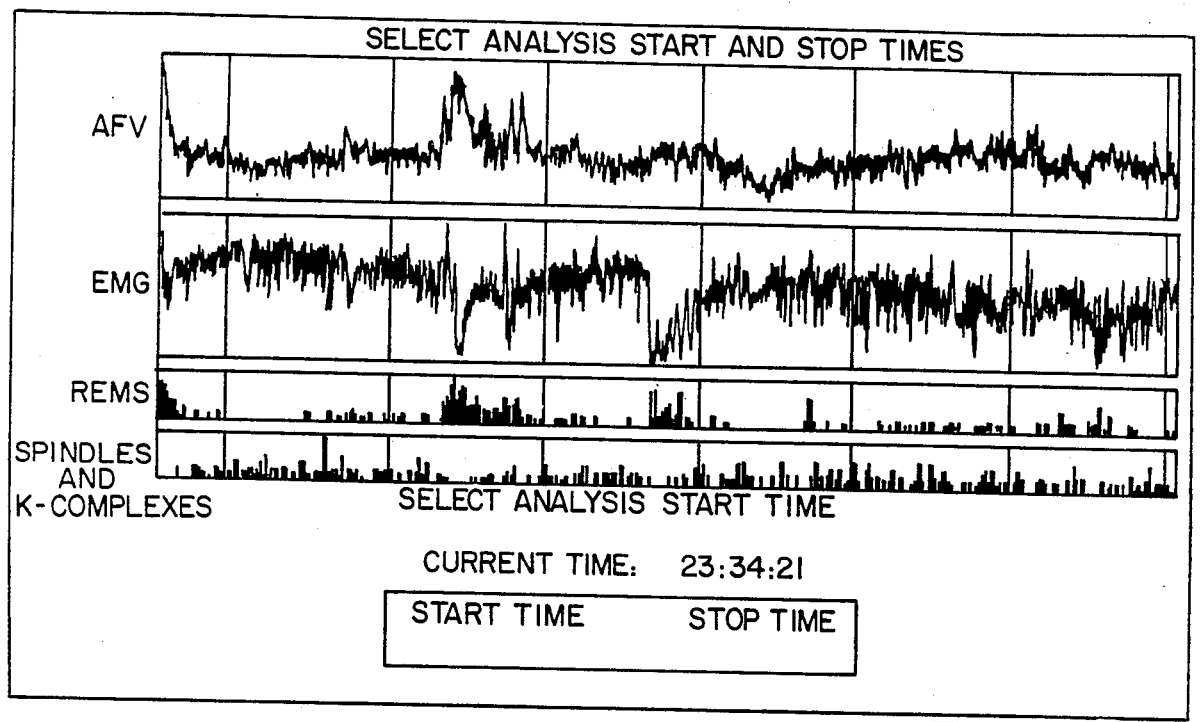

FIG. 3A presents to the operator at display and input module 17 the full succession of epoch average frequency values $AFV_e$ from the electroencephalographic signal for the entire duration of data gathering by system 11 from head 10 of a resting subject undergoing a night's sleep as the example. The vertical bars represent the beginnings of full hours. Just below the graph showing $AFV_e$ is the entire succession of the logarithm of the epoch total powers in the electromyographic signal $Log_{10}EMG_e$ simultaneously acquired from the head 10 of a subject. The next graph therebelow uses a bar graph approach to show the number of rapid eye movement events, or REM's, obtained in each epoch during this same gathering of data. Finally, the last graph shows, again using the bar graph approach, a count in each epoch of the number of sleep spindles and K-complexes which occurred in that epoch.

With this information available, the operator at display and input module 17 is prompted to supply the start time and the stop time between which waking and sleep stages are to be evaluated. Thus, if the entire record shown in FIGS. 3A contains superfluous portions at the beginning or end, these can be excised by properly choosing the start time and the stop time to eliminate these from the determination of the waking and sleep stages to be scored for the data occurring between such times.

Figure 3B:
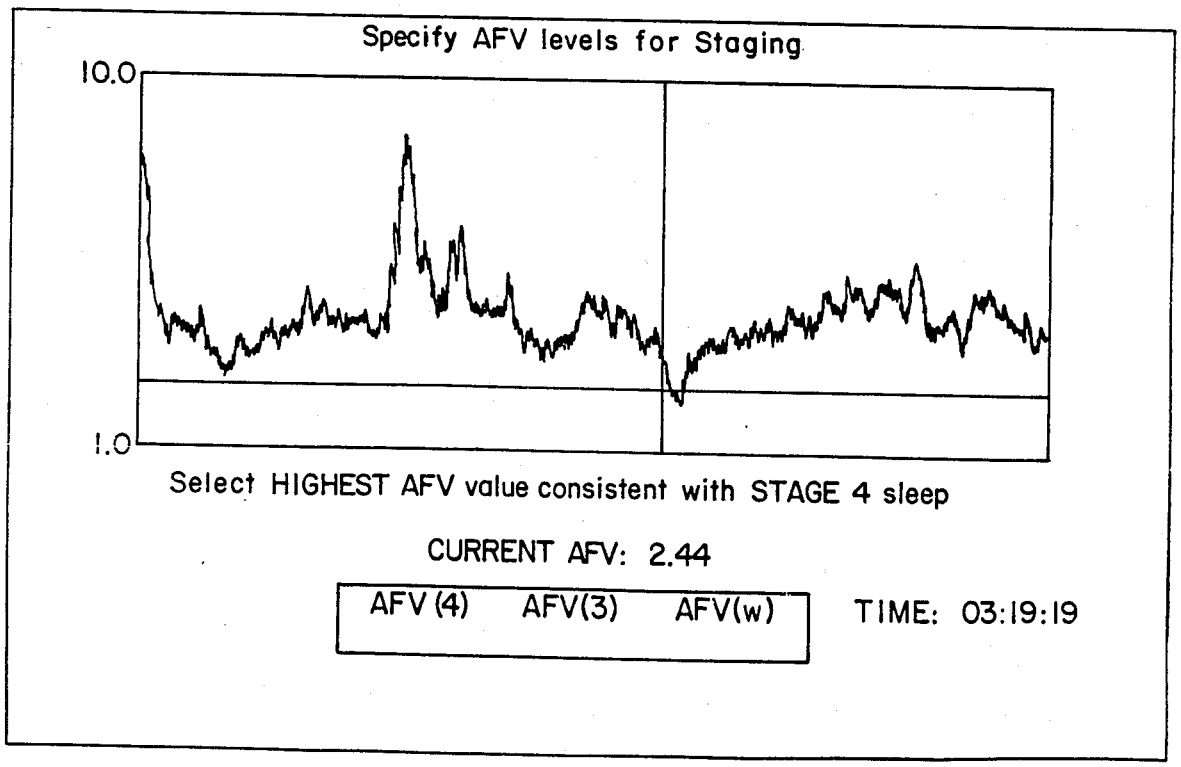

FIG. 3B illustrates the setting of the first frequency value which divides the electroencephalographic signal into portions with those portions having a frequency content below this value taken to be consistent with the type of sleep occurring in Stage 4. The operator is prompted to selected the highest $AFV_e$ value on the graph thereof consistent with Stage 4 sleep. This graph, with frequencies 1 through 10 on the ordinate axis, displays the average frequency value by epoch for the entire data gathering period between the start and stop times as shown in FIG. 3B and is an enlargement of the first graph display in FIG. 3A. A horizontal cursor can be moved up and down on the graph of $AFV_e$ as an indication means to display and input module 17 as to which value is going to be selected. Any portion of the graph of $AFV_e$ below this cursor will be taken by signal processing module 16 as having epochs containing frequencies which are consistent with Stage 4 sleep.

An operator begins by moving a vertical cursor just to the left of the lowest frequency point on the $AFV_e$ graph for a starting point, as is shown in FIG. 3B. This selects the proper epoch in which such point occurs. Thus, this epoch in the record of the electroencephalographic signal then can be found to determine whether or not this place in the electroencephalographic record is consistent with Stage 4 sleep. Such epoch could be found in a paper trace linograph record containing the records of the electroencephalographic, electromyographic and electrooculographic signals. However, the samples of these signals can be completely stored by signal processing module 16 to be much more conveniently brought to the display in display and input module 17 to provide time domain representations of these signals for review by the operator.

In either manner, the operator can sort along the electroencephalographic signal in time from this point corresponding to the starting point indicated above to find a transition point in the electroencephalographic signal that is between Stage 3 and Stage 4 sleep, if there is any Stage 4 sleep indicated to have occurred in this signal. If there is no Stage 4 sleep indicated in that signal, the horizontal cursor could be placed entirely below the $AFV_e$ tracing to indicate that no portions of the electroencephalographic signal are consistent with Stage 4 sleep. If such a transition point between Stage 3 and Stage 4 sleep is found, the vertical cursor is placed at the corresponding point on the $AFV_e$ graph and so is the horizontal cursor. This arrangement is used to inform signal processing module 16 of the setting of the first frequency value, $AFV_e4$, so that epochs of the electroencephalographic signal having average frequencies smaller than this value are consistent with Stage 4 sleep based on the corresponding point of the $AFV_e$ graph. Electroencephalographic signal epochs with average frequency content above this first frequency value will be consistent with other stages of sleep or waking.

Upon completing the finding of the transition point between Stage 4 sleep and Stage 3 sleep, the operator is next prompted to provide, as a second frequency value, the highest epoch average frequency value $AFV_e$ consistent with Stage 3 sleep. Typically, the operator will set the vertical cursor to a point somewhat higher on the graph of $AFV_e$ than where it is intersected by the first horizontal cursor. Then, the operator will have displayed on the screen of module 17 a time domain representation of the electroencephalographic, electromyographic and electrooculographic signals occurring at that point in time to the right of where the vertical cursor is located (or find them in a paper record). By moving the vertical cursor, other portions of the time domain representations of those signals at corresponding points in time can appear on the screen so that the operator can search along the electroencephalographic signal for the transition point between Stage 3 sleep and Stage 2 sleep.

Figure 3C:
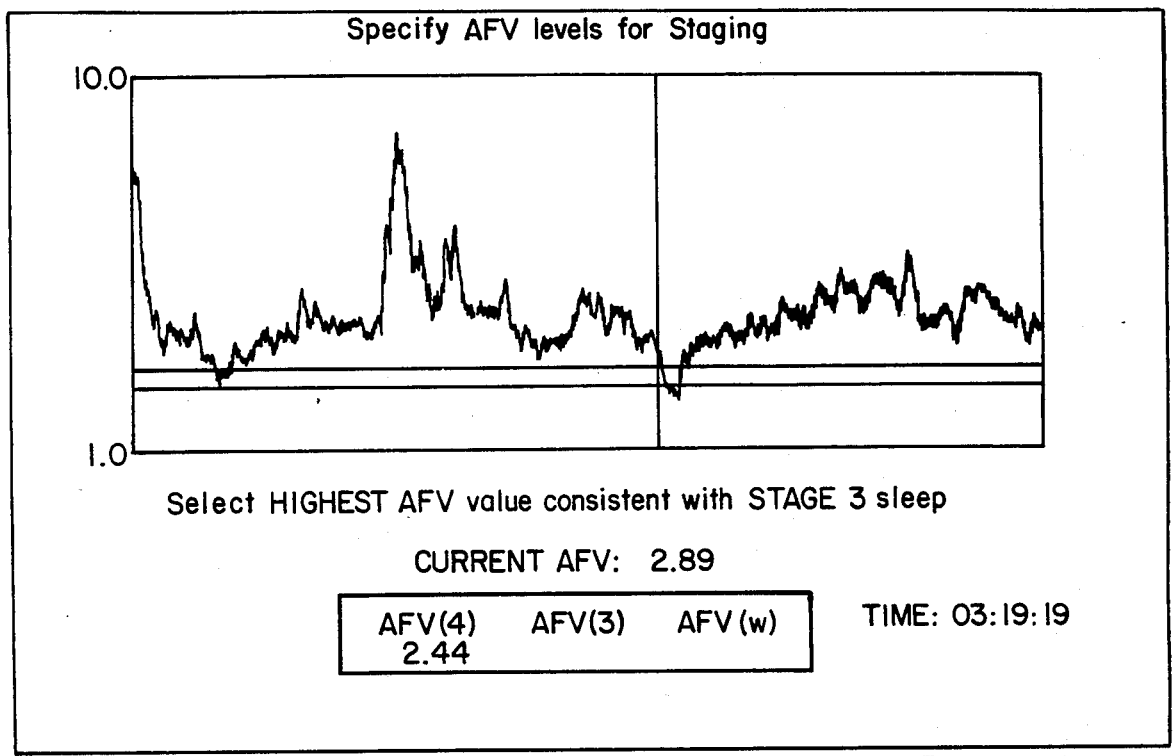

Once such a transition is found, a horizontal cursor is moved to intersect the graph of $AFV_e$ corresponding to the transition point where the vertical cursor has already been placed upon finding this point. From a keyboard, the operator indicates that this is the choice for the second frequency value, $AFV_e3$. Portions of the graph of $AFV_e$ below this second horizontal cursor and above the first horizontal cursor represent portions of the electroencephalographic signal consistent with Stage 3 sleep. Portions of the graph of $AFV_e$ above this second horizontal cursor then will represent portions of the electroencephalographic signal which are consistent with other stages of sleep. That is, the space between the first and second horizontal cursors shown in FIG. 3C represents the portions of the electroencephalographic waveform consistent with Stage 3 sleep. The frequencies selected so far as indicating transition points are also individually displayed.

As a next step, the operator must supply the information to signal processing module 16 through display and input module 17 of the frequency level above which the electroencephalographic signal is consistent with waking. To do this, the operator moves the vertical cursor to a region which he judges to be consistent with the subject being awake. Then, the operator reviews the time domain representations of the electroencephalographic, electromyographic and electrooculographic signals near this point to determine if there is a transition point to the waking state in the electroencephalographic signal. Such records can again be viewed from paper recorded tracings, but are much more conveniently viewed by having them displayed on the screen. The vertical cursor is moved along the electroencephalographic signal in time to bring different epochs in the representations of these signals to the screen until the transition point is found.

Figure 3D:
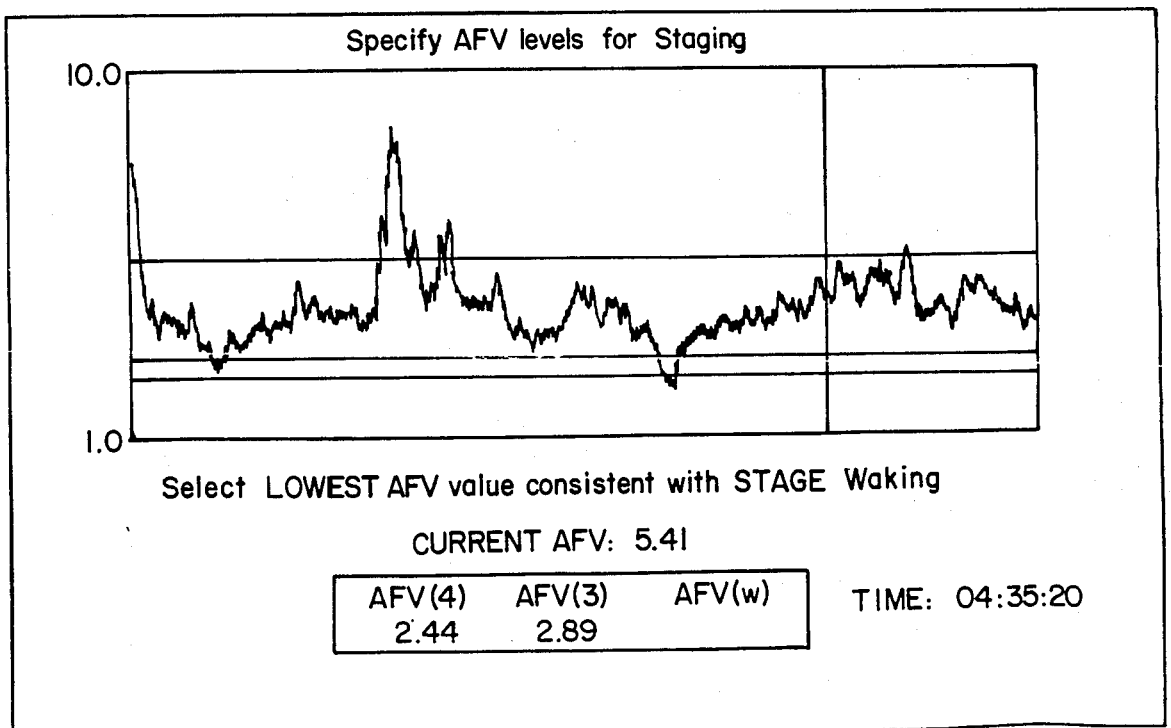

At that transition point, a third horizontal cursor is moved to intersect the time cursor set at the point on the $AFV_e$ graph corresponding to this transition point, and an input from the keyboard indicates to signal processing module 16 the value found is suitable to be the third frequency value, $AFV_ew$, which will be used to allocate those portions of the electroencephalographic signal with frequencies above this point to being considered consistent with waking. Portions of the electroencephalographic signal with frequencies below this point are consistent with one of the stages of sleep. The result is shown in FIG. 3D where all three horizontal cursors are shown in the graph of $AFV_e$. Again, the selected frequency values are also displayed. That portion of the graph of $AFV_e$ above the third cursor represents electroencephalographic signal epochs with sufficiently high average frequencies to be taken as consistent with being awake.

Figure 3E:
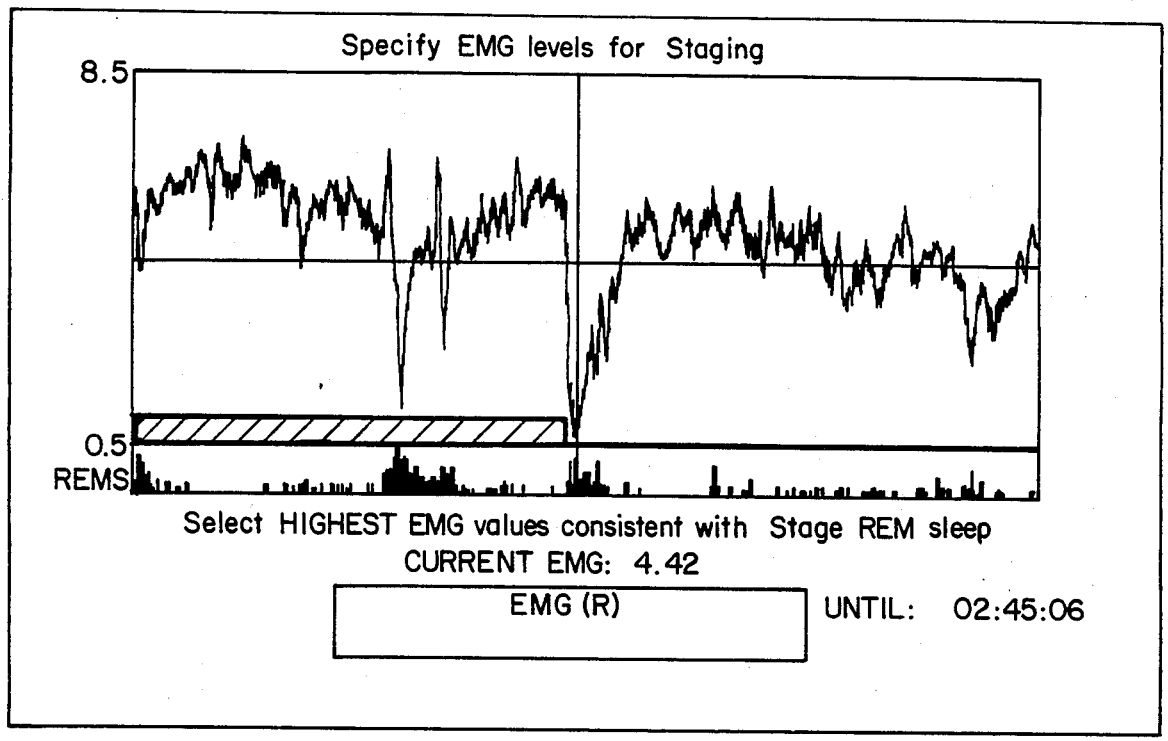

Next, to select the electromyographic signal power value (in the selected frequency range indicated above) below which portions of the electromyographic signal are consistent with Stage REM sleep, the graph of the logarithm of the total powers of the electromyographic signal is displayed on the screen of module 17 along with the bar graph of the count of rapid eye movements occurring in each epoch. This is shown in FIG. 3E where the ordinate axis of the power graph gives the logarithm to the base of 10 in the range of 0.5 to 8.5 of the total power of the electromyographic signal with respect to 1.0 mw reference voltage. Again, a vertical cursor is used to move along a time axis and a horizontal cursor to move up and down the power axis for purposes of selecting the power values. However, obtaining electromyographic signals from head 10 of a resting subject during sleep is difficult because of movement of the subject resulting in electrode contact at the submental position being poorer at some times during sleep than at other times. This results in a greater variability and inconsistency in the electromyographic signal obtained from head 10 of the subject. This requires more flexibility in selecting the power value for the electromyographic signal below which this signal is consistent with Stage REM sleep.

Such flexibility is achieved by using a split horizontal cursor which allows the use of a different power value selection in different time segments of the electromyographic total power graph over the duration of collecting data. The operator, in a typical procedure, begins by moving the vertical cursor along the graph of the electromyographic total power and then along the bar graph giving the count of rapid eye movements to a position judged to be the beginning of Stage REM sleep based on the electromyographic power levels and the extent of the occurrence of rapid eye movements. Once again, by positioning the vertical cursor the operator can obtain the time as a basis on which to go back to the time domain representations of the electromyographic and electrooculographic signals. Of course, being able to have these portions displayed on the screen of module 17 as opposed to going back to the tracing record is again much more convenient. Again, the operator can search along the electromyographic graph in time from the initially judged position to find the transition point to REM sleep. Once the operator has selected a position for the vertical cursor that separates sleep stages other than REM sleep stages from a REM sleep stage, the operator can move the portion of the horizontal cursor to the left of the vertical cursor to the selected power value on the $Log_{10}EMG_e$ graph corresponding to the transition point. In FIG. 3E, the vertical cursor has been set to a time of 2:45:06, and the horizontal cursor to the left has been set to a point below the lowest value of the total power of the electromyographic signal as the first power value, $Log_{10}EMG_eREM_1$. This has the effect of indicating to signal processing module 16 that no sleep occurred to the left of the vertical cursor which could be classified as Stage REM sleep. The display screen turns the entire portion below the horizontal cursor to the left of the vertical cursor a solid shade (represented by shading lines in FIG. 3E) to indicate the portion of the screen affected.

Figure 3F:
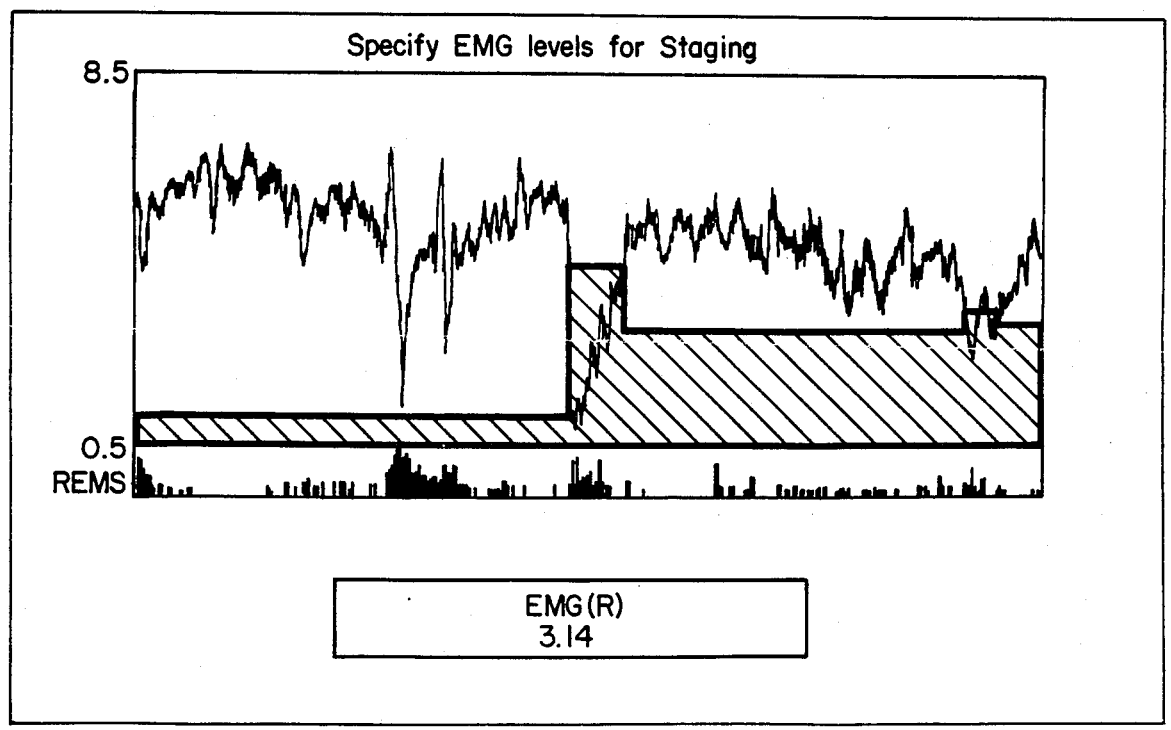

Turning to FIG. 3F, there is shown the results for the operator having followed this procedure four further times, four more time durations having been segregated through having different power values chosen therefor, $Log_{10}EMG_eREM_2$, $Log_{10}EMG_eREM_3$ and $Log_{10}EMG_eREM_4$. The turning of the screen to a solid shade at each portion below the various selected power values shows that in two places the solid shading intersects the graph of total power of the electromyographic signal indicating these have been judged to be consistent with Stage REM sleep. The last value selected is shown in a box below the graphs in FIG. 3F.

An additional scoring option is permitted in connection with the electromyographic signal $Log_{10}EMG_e$ and the finding of occurrences of Stage REM sleep. Under the rules for scoring the sleep data record into various sleep classifications, as described above, the values found for the electromyographic signal power (in a selected frequency range) in each of X time segments, or $Log_{10}EMG_eREM_x$, below which corresponding portions of the electromyographic signal are consistent with Stage REM sleep, are no more than that—just "consistent with." These values under the rules do not by themselves dictate that stage REM sleep is occurring at those times that the electromyographic signal has a power content smaller than these values. This is because various transient event occurrences, other than rapid eye movements, can have the effect that some epochs having such sufficiently low electromyographic signal powers are still to be stored as another kind of sleep.

The additional scoring option mentioned above permits ignoring such transient events altogether in these epochs having electromyographic signals with powers below the corresponding $Log_{10}EMG_eREM_x$ and scoring them all as exhibiting stage REM sleep. The operator enters a yes or no decision concerning whether to recognise these transient events in such situations in signal processing module 16 display and input module 17 to thereby provide a value for a REM TRANSIENT flag in module 16.

There are at least two reasons for this option being provided. The first is that there is a body of opinion that such transients are different from those occurring in other epochs having higher electromyographic powers (greater than the corresponding $Log_{10}EMG_eREM_x$ value) and so should be ignored in determing whether Stage REM sleep is occurring. The second reason is that there is some indication that the numbers of such transient events occurring during times that the electromyographic signal has powers below the corresponding values for $Log_{10}EMG_eREM_x$ is sometimes a measure of mental depression in the sleep subject, and that a comparison of the occurrences of Stage REM sleep, scored with and without giving effect to transient events, will provide the operator with some basis for inferring the extent of depression occurring in the subject. Such inferences may be made on the basis, for instance, of the ratio of the time of Stage REM sleep found with and without giving effect to transient events. An alternative would be the ratios of the times of Stage REM sleep found each way to the entire amount of sleep occurring in the data gathered.

The storing in a memory means, provided in signal processing module 16, of (i) these operator judgment values ($AFV_e4$, $AFV_e3$, $AFV_ew$, $Log_{10}EMG_eREM_x$), (ii) the waking or sleep stage determination found for the previous epoch, (iii) the various parameters for distinguishing transient events (sleep spindles, K-complexes, rapid eye movements, or REM's, and ordinary movement and big movement arousals), and (iv) whether transient events are to be taken into account in determining stage REM sleep (REM TRANSIENT flag value), permits the determination for each epoch in the acquired data whether waking or which of any sleep stages are represented thereby according to the decision rule procedure. The acquired data, that is, the data obtained from the electroencephalographic, electromyographic and electrooculographic signals, have the various representations thereof described above also available in signal processing module 16. These include the frequency content of the electroencephalographic signal as represented by the succession of epoch average frequency values, $AFV_e$, the power content of the electromyographic signal represented in the succession of logarithms of epoch total powers, $Log_{10}EMG_e$, and the counts in each epoch of rapid eye movements or REM's, sleep spindles and K-complexes. (Of course, the time domain representations of the sequences of samples of each of the electroencephalographic, electromyographic and electrooculographic signals have also been available, as indicated, to signal processing module 16 if they were to be displayable to the user on the display of module 17. Otherwise, paper record tracings of these signals have been available to the operator to go to directly in the absence of such access to these sequences of samples by signal processing module 16.)

The decision rules followed by signal processing module 16 must, of course, be grounded in the generally accepted rules for determining whether waking or any of the various defined sleep stages having been experienced by the resting subject during the gathering of the data provided by signal from head 10 of the subject. Since, however, the decision rules in signal processing module 16 will be applied, with reference to the acquired data, to the epoch average frequency value succession representation of the electroencephalographic signal and to the epoch total power succession representation of the electromyographic signal, the waking and sleep stage definitions must be adapted to these decision rules. The adapted sleep stage definitions or descriptions are as follows, with sleep spindles and K-complexes being interchangeable even though not mentioned:

Stage Waking: $AFV_e$ in the epoch under consideration is higher than the average frequency value, $AFV_ew$, set by the operator and the Log of the electromyographic signal level, $Log_{10}EMG_eREM_x$, set for that epoch.

Stage 1: $AFV_e$ in the epoch under consideration must be greater than $AFV_e3$ but less than $AFV_ew$. There must be no sleep spindles, K-complexes or REM's unless they occur in conjunction with movement arousals or big movement arousals, respectively. Epochs between two sleep spindles or K-complexes, separated by more than three minutes, are determined as Stage 1 epochs, as are epochs following a movement arousal occurring in an interval between two sleep spindles, and as are epochs following a movement arousal which occurs between two sleep spindles separated by less than three minutes. Sleep spindles may have K-complexes substituted therefor in the foregoing. (If the flag REM TRANSIENT has been set, transient events other than rapid eye movements will be given no effect in determining the occurrence of Stage REM sleep versus other sleep stages.)

Stage 2: $AFV_e$ in the epoch under consideration must be greater than $AFV_e3$ but less than $AFV_ew$. Either sleep spindles or K-complexes must be present in the epoch or more than half of the epoch must be between two sleep spindles separated by less than three minutes without the occurrence of any intervening movement arousals. In an exception to the requirement for $Log_{10}EMG_e$ just given, the epoch can be scored as Stage 2 even though $Log_{10}EMG_e$ is less than the value $Log_{10}EMG_eREM_x$ if more than one-half of the epoch is between two sleep spindles separated by less than three minutes without the occurrence of any intervening REM's. If a movement arousal occurs between two sleep spindles separated by less than three minutes, then all epochs prior to the movement arousal back to the first sleep spindle are scored as Stage 2 epochs, while those after the movement arousal to the second sleep spindle are scored as Stage 1 epochs. Any epoch that would otherwise be scored as Stage 2 but which occurs immediately after an epoch scored as a waking epoch will be scored as a Stage 1 epoch. Sleep spindles may have K-complexes substituted therefor in the foregoing. (If the flag REM TRANSIENT has been set, transient events other than rapid eye movements will be given no effect in determining the occurrence of Stage REM sleep versus other sleep stages.)

Stage 3: $AFV_e$ in the epoch under consideration is less than $AFV_e3$ and greater than $AFV_e4$.

Stage 4: $AFV_e$ in the epoch under consideration is less than $AFV_e4$.

Stage REM: $AFV_e$ in the epoch under consideration must be greater than $AFV_e3$, $Log_{10}EMG_e$ must be less than $Log_{10}EMG_eREM_x$ set for that epoch, and rapid eye movements must be present in the epoch or during the first three minutes following the epoch; but, however, the epoch cannot have more than one-half thereof occur between two sleep spindles or K-complexes separated by no more than three minutes without the occurrence of any intervening rapid eye movements, nor can the last big movement arousal be more recent than the last rapid eye movement. Sleep spindles may have K-complexes substituted therefor in the foregoing. (If the flag REM TRANSIENT has been set, transient events other than rapid eye movements will be given no effect in determining the occurrence of Stage REM sleep versus other sleep stages.)

With these definitions of descriptions of waking and of the possible sleep stages, the decision rules applied by signal processing module 16 are shown in the flow chart of FIGS. 4A, 4B, 4C, 4D, 4E and 4F. (The flow chart, to be shown whole, would be assembled with FIGS. 4A, 4B and 4C in a top row from left to right, and with FIGS. 4D, 4E and 4F from left to right in a bottom row with FIG. 4D directly below FIG. 4A.) The flow chart shows the steps required for determining whether an epoch under consideration should be scored as showing waking, or any of the sleep stages 1 through 4, or Stage REM. However, in some instances the decision rules require referral to events occurring in epochs on either side of the one in question as a basis for determining how the epoch under consideration should be scored. Though not shown, a K-complex can be substituted for a sleep spindle everywhere; they are interchangeable for scoring purposes.

Figure 4:
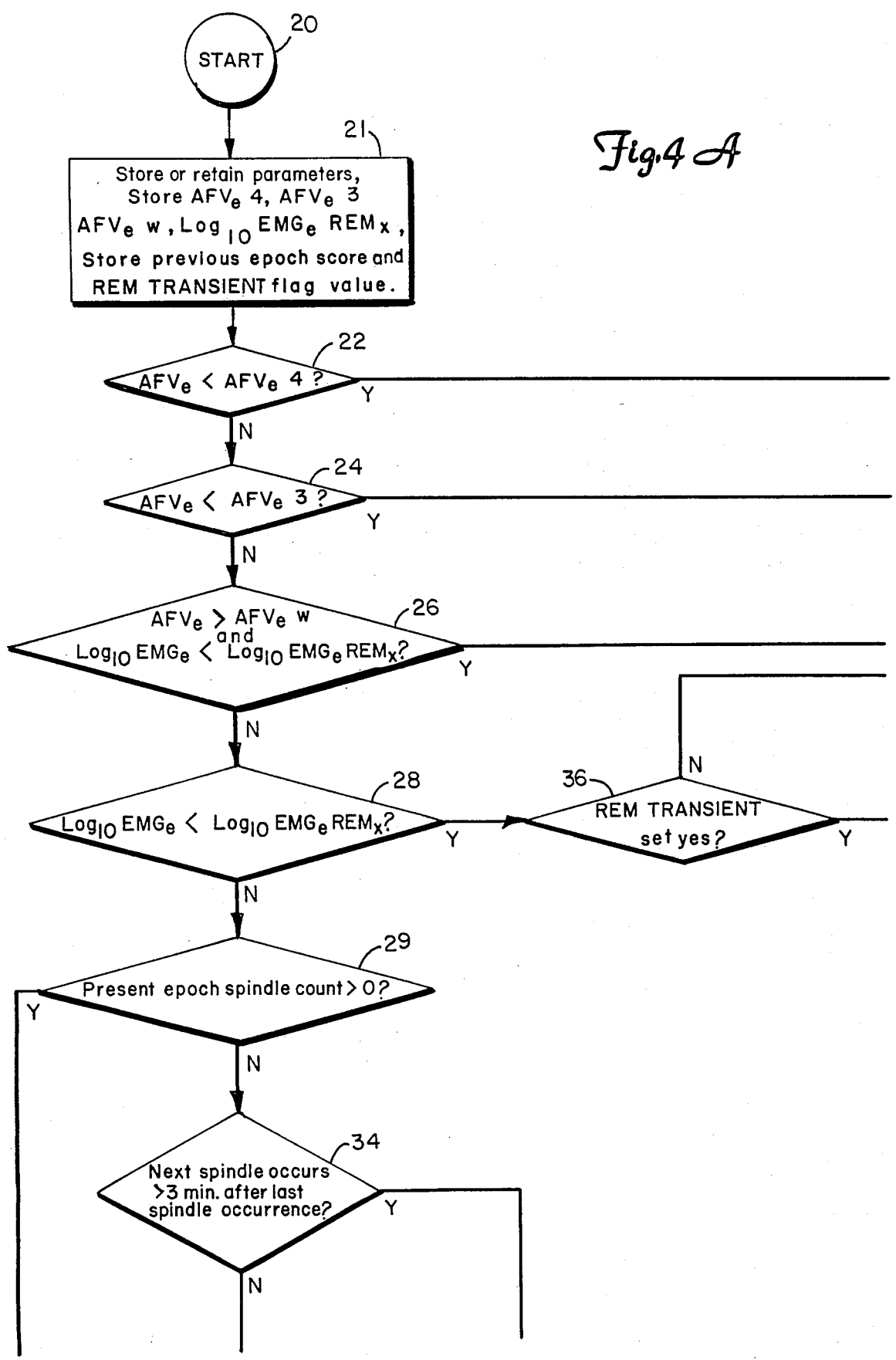

The scoring process is indicated to begin at a start circle, 20, shown in FIG. 4A. This leads to the step in the above described process, represented in FIG. 4A in a rectangular shaped box, 21, of storing (or retaining from previous usages) the various parameters used with the transient events of sleep spindles, K-complexes, movement arousals and big movement arousals, and REM's. In addition, box 21 also represents storing, in the manner described above, $AFV_e4$, $AFV_e3$, $AFV_ew$, $Log_{10}EMG_3REM_x$, and the score accorded to the previous epoch. Finally, box 21 also represents storing (or retaining from previous usages) a decision value for the REM TRANSIENT flag.

The first step taken by signal processing module 16 after such storing is to determine whether $AFV_e$ in the epoch under consideration is less than $AFV_e4$, the determination represented in FIG. 4A by a diamond shaped decision box, 22. If it is, the result is scoring the epoch as Stage 4 sleep as indicated in a circle, 23, shown in FIG. 4C.

If, on the other hand, $AFV_e$ is greater than $AFV_e4$, signal processing module 16 is directed in FIG. 4A to a further diamond decision box, 24. A determination is then required of signal processing module 16 of whether $AFV_e$ is less than $AFV_e3$. If so, the epoch is scored as representing Stage sleep, as indicated in a circle, 25, in FIG. 4C.

If $AFV_e$ is not less than $AFV_e3$, a further decision is then required of signal processing module 16 as represented in FIG. 4A in another diamond decision box, 26. If $AFV_e$ is greater than $AFV_ew$ and if $Log_{10}EMG_e$ is greater than $Log_{10}EMG_eREM_x$, the epoch is determined to represent waking, as indicated by a circle, 27, in FIG. 4C.

If, however, either of the tests in decision box 26 is not met, signal processing module 16 is directed to a further decision represented in Figure 4A in another diamond decision box, 28. This decision no longer turns on the relationship of $AFV_e$ to related parameters, but turns only on the relationship of $Log_{10}EMG_e$ being less than the pertinent $Log_{10}EMG_eREM_x$. If it is not, signal processing module 16, along a first main flow chart path branching therefrom, makes a further determination represented in another diamond decision box, 29, located in FIG. 4A.

Figure 4B:
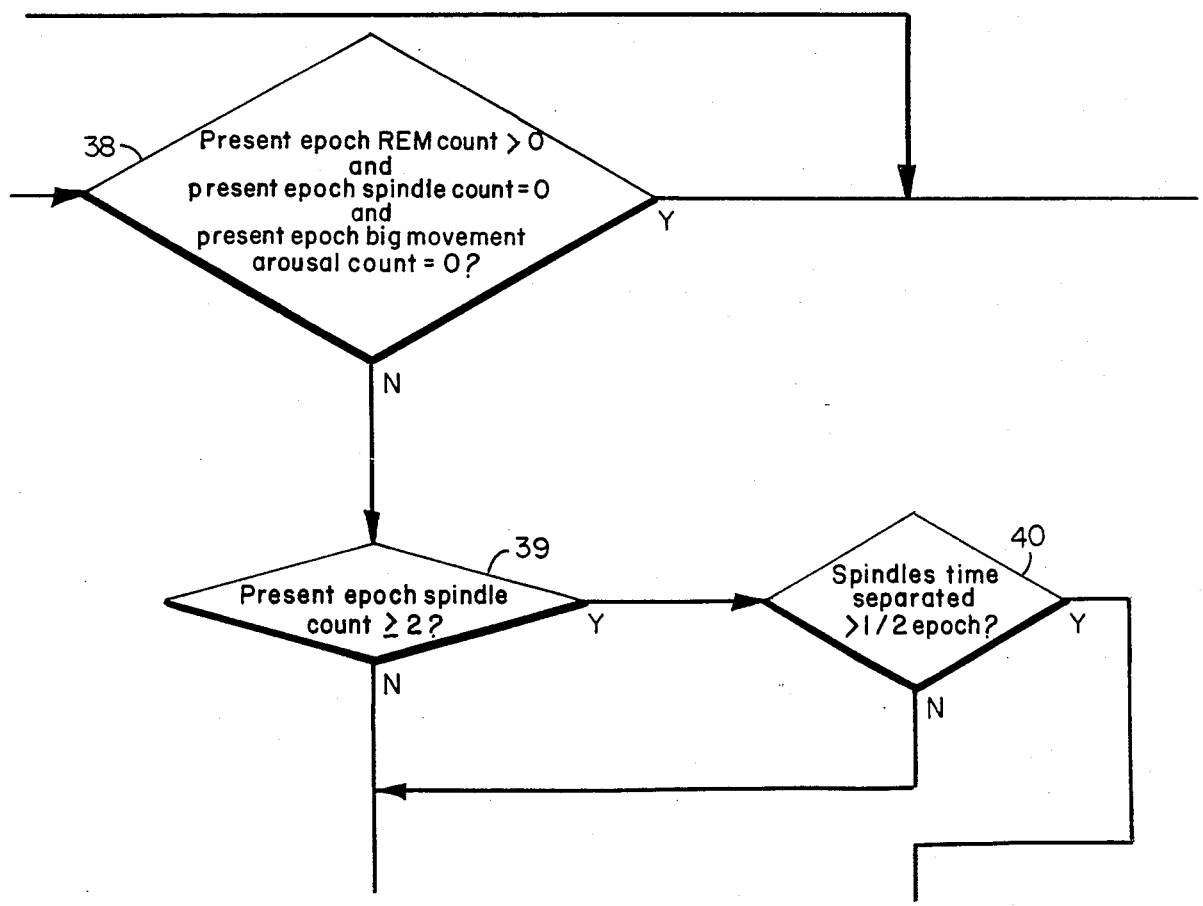
Figure 4C:
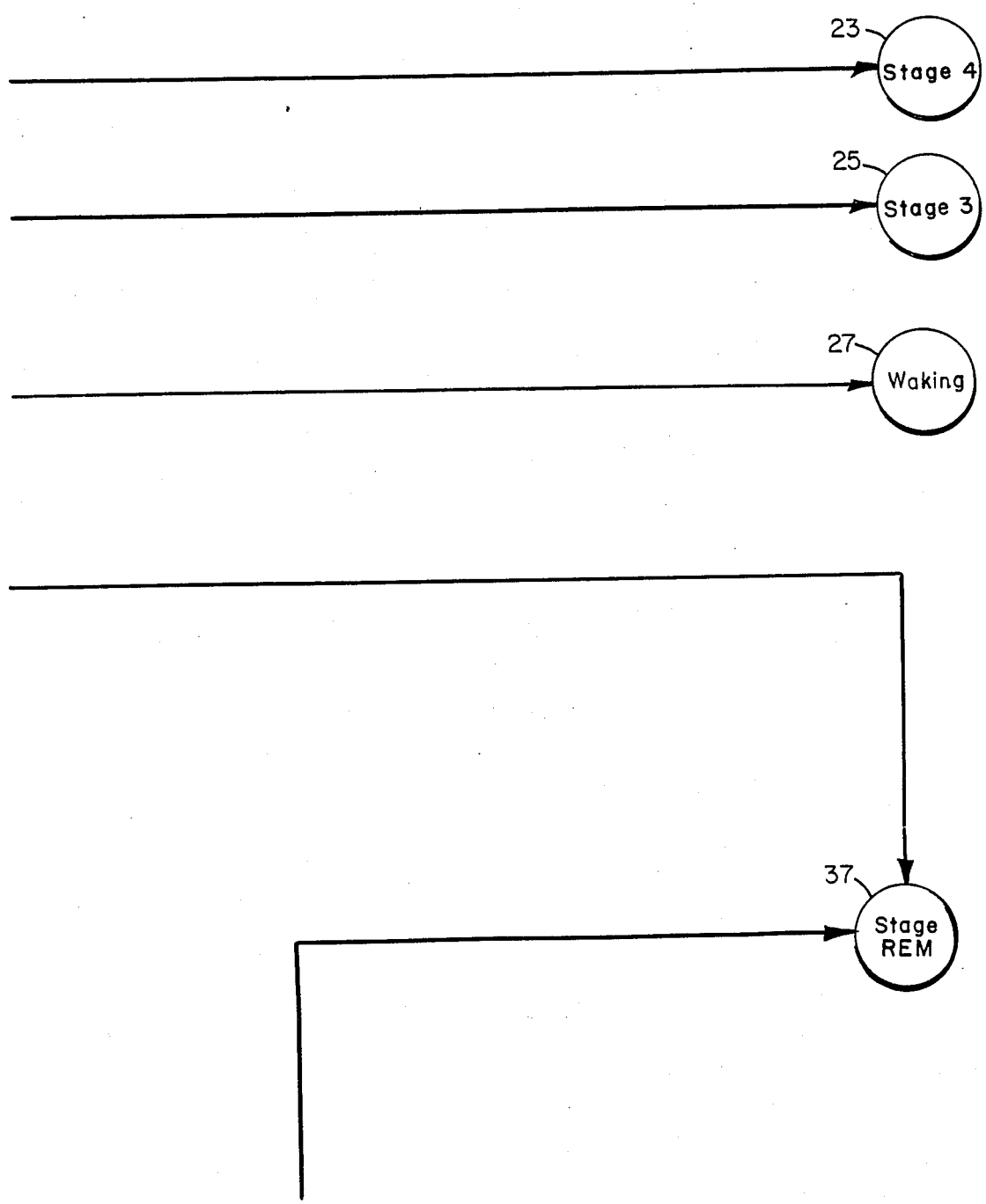
Figure 4D:
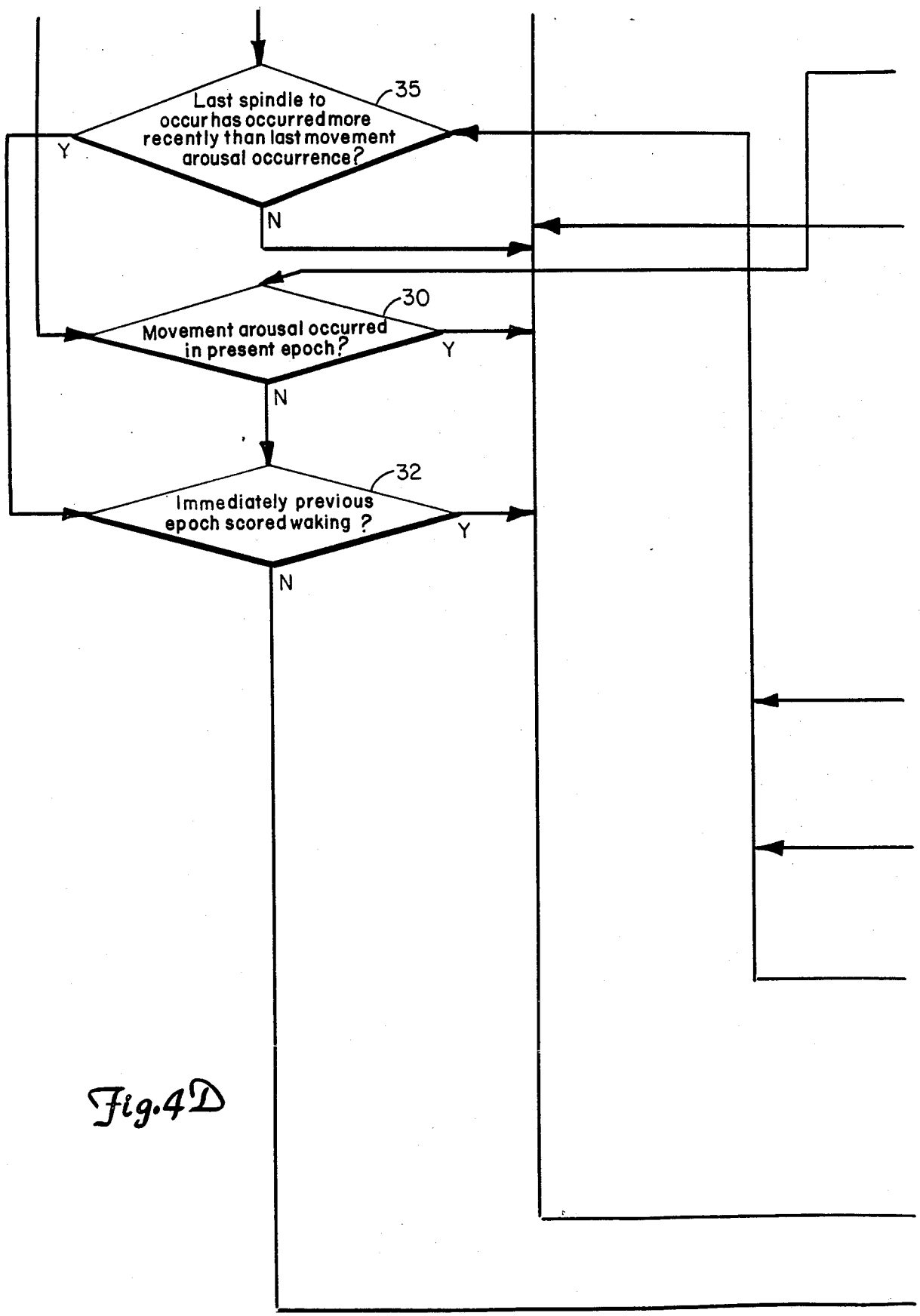

If $Log_{10}EMG_e$ is not less than the appropriate $Log_{10}EMG_eREM_x$ under box 28, and the count of sleep spindles or K-complexes in the epoch under consideration is greater than zero under box 29, then signal processing module 16 makes yet another determination under a diamond decision box, 30, in FIG. 4D, to determine whether a movement arousal occurred. If so, then the epoch is scored as representing Stage 1 sleep as indicated in a circle, 31, in FIG. 4F. If no movement arousal has occurred under box 30, a further determination must be made under a further diamond decision box, 32, shown in FIG. 4D, of whether the previous epoch was scored a waking epoch or not. If so, the present epoch is scored as representing Stage 1 sleep as indicated in circle 31. If not, then the epoch is scored as Stage 2 sleep, as indicated in a further circle, 33, in FIG. 4F.

If, however, there were no spindles determined under box 29 in the epoch under consideration, in the situation where $Log_{10}EMG_e$ is not less than $Log_{10}EMG_eREM_x$ as determined under box 28, signal processing module 16 makes another determination under a further diamond decision box, 34, in FIG. 4A. The determination represented in box 34 is whether the next sleep spindle or K-complex to occur will be separated by more than three minutes from the last one of these to occur. If so, the epoch is scored as representing Stage 1 sleep, as indicated in circle 31. If not, a further determination is required, as indicated in still another diamond decision box, 35, as shown in FIG. 4D.

The determination in box 35 is whether the last sleep spindle or K-complex to occur has occurred more recently than the last movement arousal occurrence. If it has, then again the signal processing module 16 moves to decision box 32 to determine whether the previous epoch was scored a waking epoch. If it was a waking epoch, then the epoch is taken as representing Stage 1 sleep, as indicated in circle 31. If it was not a waking epoch, then the epoch represents Stage 2 sleep indicated in circle 33. If the last sleep spindle or K-complex occurring was not more recent than the last movement arousal occurrence under box 35, then the epoch represents Stage 1 sleep, as indicated in circle 31.

The other main flow chart path branching from decision box 28 is followed by signal processing module 16 if, alternatively, $Log_{10}EMG_e$ is less than $Log_{10}EMG_eREM_x$, a branch which first requires a further determination under a diamond decision box, 36, shown in FIG. 4A. If $Log_{10}EMG_e$ is sufficiently small under box 28 to meet the test there, the REM TRANSIENT flag must be checked under box 36 to determine if the operator has decided to give effect to the other transient events in addition to rapid eye movements in assessing whether State REM sleep is occurring versus Stage 1 or Stage 2 sleep. If such transients are not to be given effect, then the epoch under consideration is immediately found to represent stage REM sleep as indicated in a circle, 37, shown in FIG. 4C.

On the other hand, if such transient events are to be taken into account, a first determination in this regard is made under another diamond decision box, 38, shown in FIG. 4B, after the finding that $Log_{10}EMG_e$ is sufficiently small to meet the test of box 28. This first determination, on finding $Log_{10}EMG_e$ small enough, is that if REM's have occurred in the epoch under consideration, i.e. the present epoch, and no sleep spindles or K-complexes or big movement arousals have occurred in such epoch, then the epoch is taken to represent Stage REM sleep. This is indicated in circle 37.

If $Log_{10}EMG_e$ is less than $Log_{10}EMG_eREM_x$, but either there are no REM's in the epoch under consideration or there are sleep spindles or big movement arousals in this epoch, signal processing module 16 makes a further determination under a further diamond decision box, 39, shown in FIG. 4B. Decision box 39 represents providing a determination of whether there are at least two sleep spindles or K-complexes (or one or more of each) occurring in this epoch, i.e. a plurality of such transient event occurrences. If there are at least two, a further determination is required as represented by another diamond decision box, 40, shown also in FIG. 4B. The determination to be made under box 40 is whether the multiple sleep spindles, or K-complexes, found to have occurred in the epoch under consideration, are separated between the points of occurrence by more than half an epoch in time. If there is such a separation in time, a further determination is made under another diamond decision box, 41, shown in FIG. 4E, of whether any REM's occurred between such spindles or K-complexes.

If there is such a half epoch time separation between these transient events with no occurrence of REM's therein as determined under box 41, there is a further determination required as to whether there was also a big movement arousal in this epoch, a determination made under a further diamond decision box, 42, shown in FIG. 4B. This determination leads to a decision that the epoch represents Stage 1 sleep as indicated in circle 31, if such a big arousal occurred and represents Stage REM sleep as indicated in circle 37 in the absence of such a big movement arousal.

If there is such a half epoch time separation between the transients, but REM's do occur therein as determined under box 41, a further determination is made under box 30 of whether a movement arousal has occurred. This determination leads to finding that the epoch represents Stage 1 sleep, as indicated in circle 31, if such an arousal occurred, but represents either such Stage 1 sleep or Stage 2 sleep, as indicated in circle 33, in the absence of such an arousal depending on whether the previous epoch was scored waking or not under box 32 in the manner previously described.

Figure 4E:
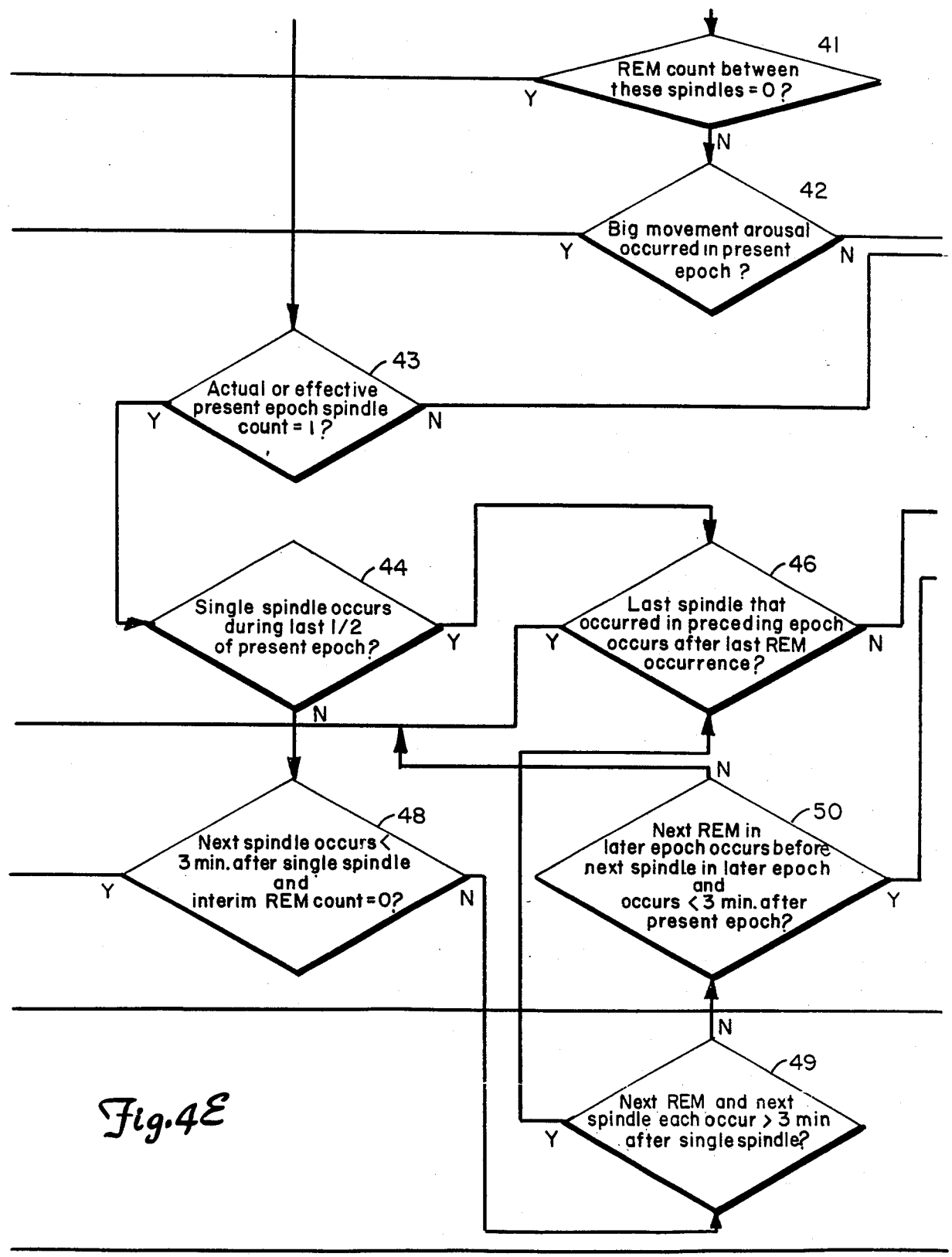

If, however, the multiple sleep spindles or K-complexes determined to be present under box 39 were not separated in time by at least half an epoch as determined under box 40, signal processing module 16 has a further determination to make under another diamond decision box, 43, shown in FIG. 4E. Signal processing module 16 also makes essentially this same determination that is set out in decision box 43 if there is determined under decision box 39 that there were not two or more sleep spindles in the epoch.

Thus, decision box 43 determines, in the instance of being invoked by signal processing module 16 directly from decision box 39 in the absence of finding two sleep spindles or K-complexes in the epoch, whether there was one sleep spindle or K-complex in the epoch. If so, signal processing module 16 undertakes another determination under a further diamond decision box, 44, shown in FIG. 4E. If, however, there were no sleep spindles or K-complexes found under box 43, signal processing module 16 branches to an alternative further diamond decision box, 45, shown in FIG. 4F.

If decision box 43, however, is instead invoked by signal processing module 16 from box 40 after making the determination under box 40 that the two sleep spindles or K-complexes found in the epoch under consideration were not separated by at least half the time of the epoch, there is then made what amounts to a directed determination under decision box 43 that there is only one sleep spindle effectively occurring in this epoch, this being the last of the two or more sleep spindles or K-complexes found under box 39. In any event, if under box 43 there is either one actual sleep spindle or K-complex found in the epoch under consideration or a directed determination that effectively only one occurs in such epoch, signal processing module 16 branches to determining under decision box 44 whether that sleep spindle or K-complex occurred in the last half of this epoch.

A determination that a single spindle has occurred in the last half of the present epoch leads to a further determination under another diamond decision box, 46, shown in FIG. 4E, as to whether the last spindle that occurred in a preceding epoch also occurred after the occurrence of the last REM. If so, there is a check to determine whether this last spindle to occur also occurred more recently than the last movement arousal under decision box 35. The present epoch will then be determined under box 35, and possibly under boxes 30 or 32, or both, to represent either Stage 1 or Stage 2 sleep in the manner previously described.

Figure 4F:
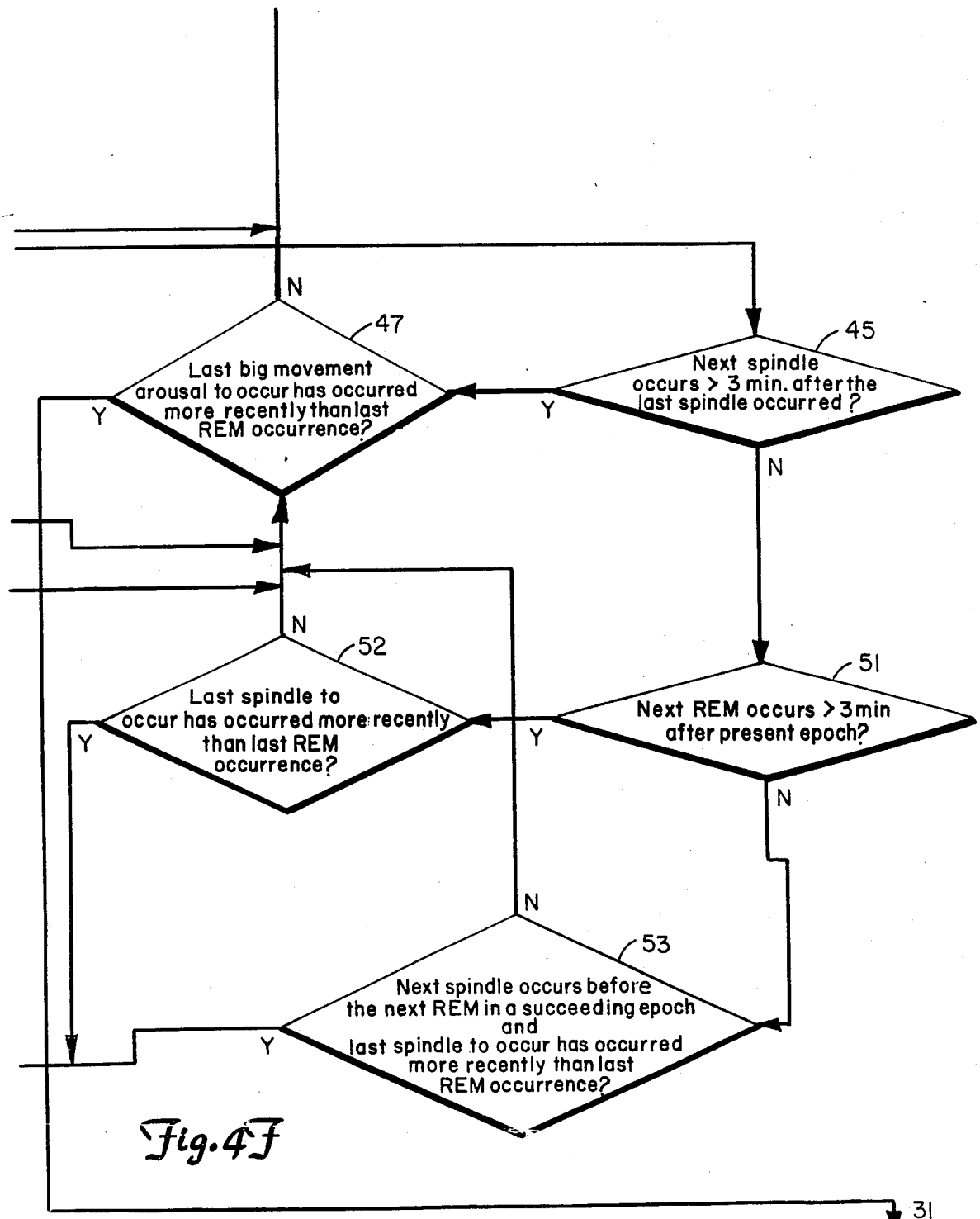

If, on the other hand, the last spindle that occurred in the preceding epoch is not found under box 46 to have occurred after the occurrence of the last REM, in the situation where a single spindle is taken to have occurred in the present epoch under box 43 and to have occurred in the last half of such epoch under box 44, signal processing module 16 will make a further determination under another diamond decision box, 47, shown in FIG. 4F. This determination is whether the last big movement arousal occurred more recently than the last REM occurrence. If so, the present epoch will be scored as representing Stage 1 sleep, as indicated in circle 31. If not, the epoch will be scored as representing Stage REM sleep, as indicated in circle 37.

Returning now to box 44, and the situation where an actual or effective single spindle has been found to occur in the present epoch under box 43 but where it does not occur in the last half of such epoch, a further determination is required of signal processing module 16 under another diamond decision box, 48, shown in FIG. 4E. The determination here is whether this actual or effective single sleep spindle or K-complex, having occurred in the first half of the present epoch, has also occurred within three minutes of the next sleep spindle or K-complex occurring thereafter and without any REM's occurring in the interim time interval between them. If both these conditions, concerning the timing of the succeeding sleep spindle or K-complex and lack of interim REM's, are met for the single sleep spindle or K-complex occurring in the present epoch, such epoch is then checked to determine whether this single spindle or K-complex occurred more recently than the last movement arousal under decision box 35. The epoch will then be determined under decision box 35, and possibly under decision boxes 30 or 32 or both, to represent either Stage 1 or Stage 2 sleep in the manner previously described.

If either of the two conditions of decision box 48 has not been met, that is, that the next sleep spindle or K-complex occurs more than three minutes after the single spindle or K-complex found under box 43, (which was found to occur in the first half of the present epoch under box 44) or that the interim REM count is greater than zero, signal processing module 16 must make a further determination under another diamond decision box, 49, shown in FIG. 4E. This determination is whether any of the next occurrences of a REM, or a spindle or a K-complex, which occurs after the occurrence of the present epoch single spindle or K-complex, has also occurred more than three minutes thereafter. If each such next occurrence has been more than three minutes afterward, signal processing means 16 moves on to a determination under decision box 46 as to whether the last spindle that occurred in a preceding epoch had also occurred after the last REM occurred. If so, the epoch will then be determined under decision box 35, and possibly under decision box 30 or 32, or both, to represent either Stage 1 sleep, as indicated in circle 31, or Stage 2 sleep, as indicated in circle 33, in the manner previously described. If the last spindle in a preceding epoch has not occurred after the last REM, the epoch will be determined under decision box 47 to represent either Stage 1 sleep, as indicated in circle 31, or Stage REM sleep as indicated in circle 17, in the manner previously described.

If, however, the occurrences of any of the next REM, and the next sleep spindle or K-complex, is within three minutes after the single spindle found under box 43 (found to occur in the first half of the present epoch under box 44), as determined under boxes 48 and 49, decision means 16 will make a further determination under another diamond decision box, 50, shown in FIG. 4E, rather than under box 46. Under box 50, the determination is whether the next REM in a later epoch ocurs before the next sleep spindle or K-complex in a later epoch, and occurs less than three minutes after the present epoch. If the next REM has so occurred, the epoch will then be determined under decision box 47 to represent either Stage 1 sleep, as indicated in circle 31, or Stage REM sleep, as indicated in circle 37, in the manner previously described. If the next REM does not meet this test under box 50, the present epoch will be scored under box 35, and possibly decision boxes 30 or 32, or both, as representing either Stage 1 sleep, as indicated in circle 31, or Stage 2 sleep, as indicated in circle 33, in the manner previously described.

The situation where more than two spindles or K-complexes occur in the present epoch as determined under box 39 was first described above. Further, the description of the situation where just one sleep spindle or K-complex has been found in the present epoch, either actually or effectively, has just been completed. There remains the one further possibility of there having been neither sleep spindle nor K-complex found to have occurred in the present epoch under box 43. As was indicated above, in that situation signal processing module 16 goes on to make a further determination under box 45 of whether the spindle in the next epoch occurs more than three minutes after the last spindle in a preceding epoch. If it has, the epoch is scored under decision box 47 as representing either Stage 1 sleep, as indicated in circle 31, or Stage REM sleep, as indicated in circle 37, in the manner previously indicated. On the other hand, if the present epoch having no spindles or K-complexes, as determined under box 43, has the next sleep spindle or K-complex in a succeeding epoch occur less than three minutes after the last spindle or K-complex in a preceding epoch, signal processing module 16 goes on to make a further determination under another diamond decision box, 51, as shown in FIG. 4F. The determination there to be made is whether the next REM occurs more than three minutes after the present epoch. If so, a further determination is undertaken under another diamond decision box, 52, also shown in FIG. 4F. The decision there is whether the last spindle or K-complex to occur has occurred more recently than the last REM which has occurred. If so, the present epoch is scored under box 35, and possibly under decision boxes 30 or 32, or both, as representing either Stage 1 sleep, as indicated in circle 31, or Stage 2 sleep, as indicated in circle 33, in the manner previously described. If the next REM to occur does so more than three minutes after the present epoch, but the last spindle to occur has not occurred more recently than the last REM to occur, the present epoch is scored under decision box 47 as representing either Stage 1 sleep, as indicated in circle 31, or Stage REM sleep, as indicated in circle 37, in the manner previously described.

The determination of there being no spindles in the present epoch under box 43, that the next spindle or K-complex occurs within three minutes after the last spindle under box 45, and that the next REM occurs within three minutes after the present epoch under box 51 leads to signal processing module 16 making a further decision under another diamond decision box, 53, shown in FIG. 4F. If the next spindle to occur then occurs before the next REM in a succeeding epoch and the last spindle to occur has occurred more recently than the last REM has occurred, the present epoch is scored under box 35, and possibly boxes 30 or 32, or both, as representing either Stage 1 sleep, as indicated in circle 31, or Stage 2 sleep, as indicated in circle 33, in the manner previously described.

If the tests of box 53 are not met in the this circumstance, however, the present epoch is scored under box 47 as representing Stage 1 sleep, as indicated in circle 31, or Stage REM sleep, as indicated in circle 37, in the manner previously described under box 47.

This completes the description concerning how transient events in addition to rapid eye movements are given effect in the scoring of an epoch as to sleep type if the electromyographic signal power $Log_{10}EMG_e$ is less than a selected value in the appropriate time segment, $Log_{10}EMG_3REM_x$, and the REM TRANSIENT flag is set to give effect to such transients. As indicated, the classification is ordered primarily by the numbers of occurrences of spindles or K-complexes occurring in the present epoch with these being divided into three classes of two or more such transient events, one such transient event or no such transient events. As indicated, further transient events involving arousals and certain timing constraints also affect the scoring.

The frequent use of a three-minute duration in the previous decision rules occurs because of its use in the generally accepted sleep scoring rules referred to above. However, this is not universally accepted, and therefore may be varied in signal processing module 16 through input module 17 depending on the operator's preference. Also, though not shown in the decision rules, the final determination of having really passed through a stage change to being in a different stage may be affected by the number of epochs in which the stage has been successively scored. In other words, the operator may require in signal processing module 16 that a stage change be scored only if it happens in a sufficient number of successive epochs to thereby remove any evanescent data effects which could lead to temporarily scoring a stage of sleep which would then appear as an anomaly.

Figure 5:
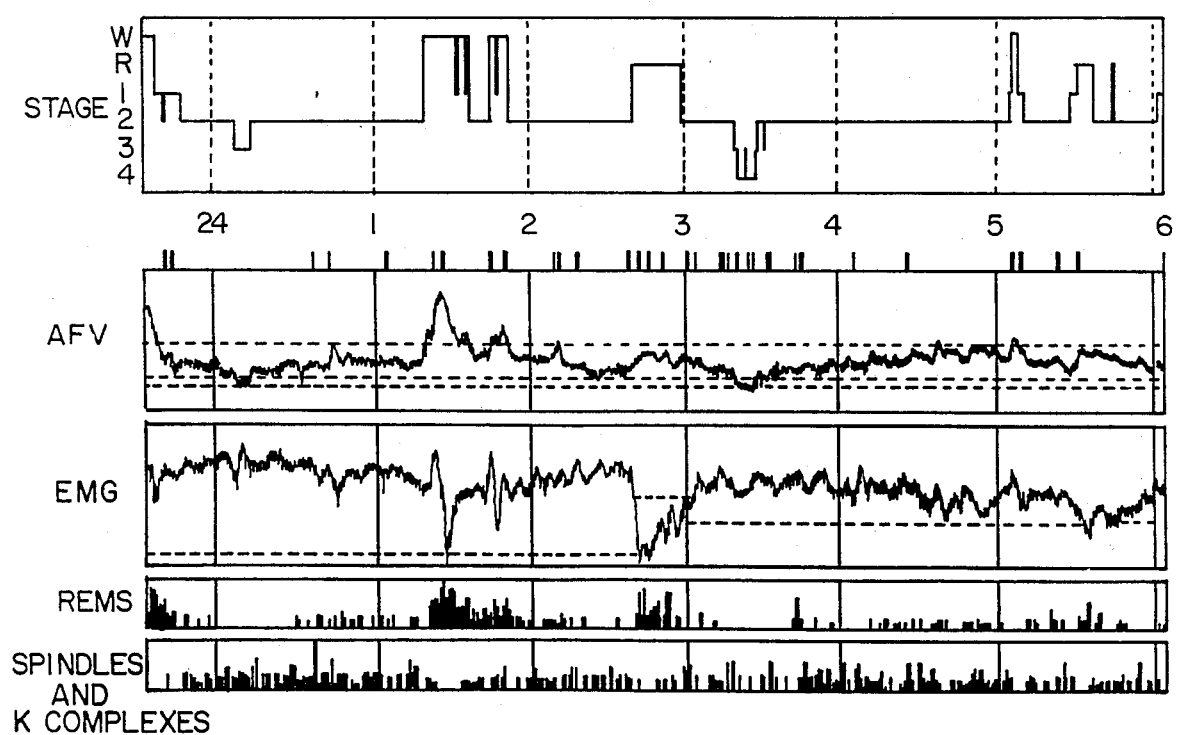
FIG. 5 shows a summary display provided by the system of FIG. 1C.

Signal processing module 16, in having access to the stored values shown at the beginning of the flow chart in FIG. 4A, and to the frequency content representation of the electroencephalographic signal, and to the power content of the electromyographic signal, applies the foregoing decision rules to determine the stages of sleep and to provide other data. The results can be displayed in display and input module 17, an example of which is shown in FIG. 5 on a display screen from that module. The display there continues the example shown in FIGS. 3A through 3F.

The upper graph has on the ordinate axis thereof, from top to bottom, the waking state, and the various sleep stages beginning with Stage REM represented by an R, and followed downward by Stage 1, Stage 2, Stage 3 and Stage 4. A broken line graph arrangement is used, spread over the abscissa axis representing the clock hours approximately slept based on a twenty-four hour clock, to show the scored waking and sleeping stages. The vertical-lines represent the beginnings of each hour.

Below the graph of waking and sleep stages, is again presented the graph of the average frequency value of each epoch occurring during the gathering of data, the vertical lines there again representing the beginnings of clock hours. The three horizontal dotted lines represent, from bottom up, $AFV_e4$, $AFV_e3$, and $AFV_ew$. On the top of this graph there is presented a series of vertical marks spread across the time axis. These are event marks which an operator can add either during monitoring the sleep data gathering session or by noting them during reviews of the time domain representations of the electroencephalographic, electromyographic and electrooculographic signals.

The next graph down is that of the logarithm to the base 10 of the total powers of the electromyographic signal also in each such epoch. Vertical hour lines are again shown. The various horizontal-lines represent the values of $LOG_{10}EMG_eREM_x$ as set over various time durations across the abscissa axis of this graph.

The final two graphs are bar graphs showing the counts of rapid eye movements or REM's in each epoch, and the counts of sleep spindles and K-complexes in each epoch. The heights of the bars represent counts of these events on a relative basis—the bars are adjusted in height for the actual counts found so that the height of the largest bar present is always at the full height possible in the display.

Several other parameters of interest to the operator can be selectively displayed, or a permanent record made thereof, or both, in display and input module 17 at the choice of the operator. Thus, clock times of going to bed and rising, total time in bed, total sleeping time, distribution of waking period times, and the like can be displayed. Various derived parameters from such data can also be displayed. In addition, figures on the sleep stage time distributions can also be provided. Other information can, of course, be entered by the operator at display and input module 17 for display or permanent recording.

Although the present invention has been described with reference to preferred embodiments, workers skilled in the art will recognize that changes may be made in form and detail without departing from the spirit and scope of the invention.

What is claimed is:

1. A method of determining whether waking or any of a plurality of defined types of sleep including first, second, third, fourth and fifth types of sleep occur in data gathered from a subject, said determinations being made based on such data gathered and various criteria, said method comprising:
   obtaining electroencephalographic signal data and electromyographic signal data from said subject;
   providing a representation of frequency content of said electroencephalographic signal data and presenting said electroencephalographic frequency content representation on a display means;
   providing a representation of signal strength of said electromyographic signal data and presenting said electromyographic signal strength representation on said display means;
   providing selected frequency and signal strength values at least one of which is greater than values of a portion and less than values of another portion of a corresponding one of said electroencephalographic frequency content representation and said electromyographic signal strength representation; and
   determining, based on said electroencephalographic signal data and said electromyographic signal data and on said selected frequency and signal strength values, whether waking or which of any of said types of sleep have been experienced by said subject during said obtaining of said electroencephalographic signal data and electromyographic signal data.

2. The method of claim 1 further comprising obtaining electrooculographic signal data from said subject and providing a representation of occurrences of selected eye movements indicated in said electrooculographic signal data.

3. The method of claim 2 wherein said obtaining of said electroencephalographic signal data, said electromyographic signal data, and said electrooculographic signal data comprises acquiring a first sequence of consecutive samples of amplitude values of said electroencephalographic signal data taken at a rate sufficient to represent that signal, acquiring a second sequence of consecutive samples of amplitude values of said electromyographic signal data taken at a rate sufficient to represent that signal, and acquiring a third sequence consecutive samples of amplitude values of said electrooculographic signal data taken at a rate sufficient to represent that signal.

4. The method of claim 3 wherein said first sequence of consecutive samples also comprises a plurality of successive, selected first sequence subsequences, said second sequence also comprises a plurality of successive, selected second sequence subsequences, and said third sequence of consecutive samples also comprises a plurality of successive, selected third sequence subsequences, and wherein said method further comprises forming a first succession of frequency domain power spectra with there being one of said frequency domain power spectra in said first succession thereof formed for each of selected ones of said first sequence subsequences, forming a second succession of frequency domain power spectra with there being one of said frequency domain power spectra in said second succession thereof formed for each of selected ones of said second sequence subsequences, forming a third succession of frequency domain power spectra with there being one of said frequency domain power spectra formed for each of selected ones of said third sequence subsequences.

5. The method of claim 4 wherein said method further comprises forming a succession of weighted averages with there being one of said weighted averages in said succession thereof found for those frequencies present in each of said first succession of frequency domain power spectra through finding the products of frequencies represented in a frequency domain power spectrum and spectral power at those frequencies divided by a totality of spectral powers of those frequencies represented in that said spectrum, and determining a succession of total powers with there being one of said total powers determined for each said frequency domain power spectrum in said second succession thereof, determining for each of selected said first sequence subsequences whether any sleep spindles or K-complexes have occurred therein, and determining for each of selected said third sequence subsequences whether any rapid eye movements have occurred therein.

6. The method of claim 5 further comprising determining selectively from each simultaneously acquired said first sequence subsequence and said second sequence subsequence jointly, and from each simultaneously acquired said second sequence subsequence and said third sequence subsequence jointly, whether an indication of a movement arousal is present.

7. The method of claim 5 further comprising forming a succession of epoch average frequency values with each said epoch average frequency value in said succession thereof comprising an arithmetic average of a selected plurality of said weighted averages from said succession thereof, and forming a succession of epoch average total powers with each said epoch average total power in said succession thereof comprising an arithmetic average of a selected plurality of said total powers from said succession thereof.

8. The method of claim 7 further comprising presenting said eye movement occurrence representation on said display means.

9. The method of claim 2 wherein said determining is preceded at least in part by finding occurrences of sleep spindles and K-complexes in said electroencephalographic signal data, and finding occurrences of rapid eye movements in said electrooculographic signal data, and wherein said determining is further based on said occurrences.

10. The method of claim 9 wherein said finding of occurrences further comprises finding occurrences of movement arousals selectively indicated jointly in said electromyographic signal data and said electroencephalographic signal data, and jointly in said electromyographic signal data and said selectrooculographic signal data, and wherein said determining is further based on such occurrences.

11. The method of claim 10 wherein said determining further comprises determining any incidences of at least one type of said types of sleep based both on giving effect to said occurrences and on giving no effect to said occurrences other than occurrences of rapid eye movements, followed by comparing incidences of that one type of sleep as determined on each basis to one another.

12. The method of claim 9 wherein said determining further comprises determining any incidences of at least one type of said types of sleep based both on giving effect to said occurrences and on giving no effect to said occurrences other than occurrences of rapid eye movements, followed by comparing incidences of that one type of sleep as determined on each basis to one another.

13. The method of claim 1 wherein said obtaining of said electroencephalographic signal data and said electromyographic signal data comprises acquiring a first sequence of consecutive samples of amplitude values of said electroencephalographic signal data taken at a rate sufficient to represent that signal, and acquiring a second sequence of consecutive samples of amplitude values of said electromyographic signal data taken at a rate sufficient to represent that signal.

14. The method of claim 13 wherein said first sequence of consecutive samples also comprises a plurality of successive, selected first sequence subsequences, and said second sequence also comprises a plurality of successive, selected second sequence subsequences, and wherein said method further comprises forming a first succession of frequency domain power spectra with there being one of said frequency domain power spectra in said first succession thereof formed for each of selected ones of said first sequence subsequences, and forming a second succession of frequency domain power spectra with there being one of said frequency domain power spectra in said second succession thereof formed for each of selected ones of said second sequence subsequences.

15. The method of claim 14 wherein said method further comprises forming a succession of weighted averages with there being one of said weighted averages in said succession thereof found for those frequencies present in each of said first succession of frequency domain power spectra through finding the products of frequencies represented in a frequency domain power spectrum and spectral power at those frequencies divided by a totality of spectral powers of those frequencies represented in that said spectrum, and determining a succession of total powers with there being one of said total powers determined for each said frequency domain power spectrum in said second succession thereof.

16. The method of claim 15 further comprising determining from each simultaneously acquired said first sequence subsequence and said second sequence subsequence jointly whether an indication of a movement arousal is present.

17. The method of claim 15 further comprising forming a succession of epoch average frequency values with each said epoch average frequency value in said succession thereof comprising an arithmetic average of a selected plurality of said weighted averages from said succession thereof, and forming a succession of epoch average total powers with each said epoch average total power in said succession thereof comprising an arithmetic average of a selected plurality of said total powers from said succession thereof.

18. The method of claim 1 wherein said providing of said electroencephalographic frequency content representation comprises obtaining a frequency power spectrum of said electroencephalographic signal data for a period of time and forming a weighted average of frequencies present in that spectrum by finding a totality of products of frequencies represented in said spectrum and spectral powers at those frequencies divided by a totality of spectral powers of those frequencies represented in said spectrum.

19. The method of claim 18 wherein said providing of said electromyographic signal strength representation comprises obtaining a logarithm of that signal strength present occurring in said electromyographic signal data.

20. The method of claim 19 further comprising obtaining electrooculographic signal data from said subject, providing a representation of numbers of occurrences of selected eye movements indicated in said electrooculographic signal data, and presenting said eye movement representation of numbers of occurrences on said display means.

21. The method of claim 1 wherein said providing of said electromyographic signal strength representation comprises obtaining a logarithm of that signal strength present in said electromyographic signal data.

22. The method of claim 21 wherein said signal strength is found by determining that power contained in at least a portion of said electromyographic signal data.

23. The method of claim 1 wherein said providing of said selected frequency and signal strength values comprises:
   entering into a memory means a selected first frequency value chosen such that taking a portion of said electroencephalographic frequency content representation having frequency values related in a selected manner to said first frequency value, if any, is consistent with said fourth type of sleep;
   entering into said memory means a selected second frequency value chosen such that taking a portion of said electroencephalographic frequency content representation having frequency values related in a selected manner to said second frequency value and to said first frequency value, if any, is consistent with said third type of sleep;
   entering into said memory means a selected third frequency value chosen such that taking a portion of said electroencephalographic frequency representation having frequency values related in a selected manner to said third frequency value is consistent with said waking; and entering into said memory means a selected first signal strength value chosen such that taking a portion of said electromyographic signal strength representation having signal strength values related in a selected manner to said first signal strength value, if any, is consistent with said fifth type of sleep.

24. The method of claim 23 wherein said entering into a memory means of a selected first frequency value comprises estimating along said electroencephalographic frequency content representation an initial first frequency value, reviewing representations of portions of said electroencephalographic signal data from which those portions of said electroencephalographic frequency content representation having values near said initial first frequency value were obtained, determining wherein said electroencephalographic signal data transition region occurs between a portion of said electroencephalographic signal data consistent with said fourth type of sleep and another portion thereof consistent with said third type of sleep, and entering in said memory means as said selected first frequency value that frequency value at which said transition region occurs.

25. The method of claim 24 wherein said reviewing of representations comprises displaying said representations of portions of said electroencephalographic signal data on said display means.

26. The method of claim 24 further comprising obtaining electrooculographic signal data from said subject, providing a representation of occurrences of selected eye movements indicated in said electrooculographic signal data, and presenting said eye movement occurrence representation on said display means, and wherein said reviewing of representations of portions of said electroencephalographic data is accompanied by reviewing representations of simultaneously obtained portions of said electromyographic signal data and said electrooculographic signal data.

27. The method of claim 23 wherein said entering into a memory means of a selected second frequency value comprises estimating along said electroencephalographic frequency content representation an initial second frequency value, reviewing representations of portions of said electroencephalographic signal data from which those portions of said electroencephalographic frequency content representation having values near said initial second frequency value were obtained, determining where in said electroencephalographic signal data a transition region occurs between a portion of said electroencephalographic signal data consistent with said third type of sleep and another portion thereof consistent with other types of sleep excluding said fourth type of sleep, and entering in said memory means as said selected second frequency value that frequency value at which said transition region occurs.

28. The method of claim 27 wherein said reviewing of representations comprises displaying said representations of portions of said electroencephalographic signal data on said display means.

29. The method of claim 27 further comprising obtaining electrooculographic signal data from said subject, providing a representation of occurrences of selected eye movements indicated in said electrooculographic signal data, and presenting said eye movement occurrence representation on said display means, and wherein said reviewing of representations of portions of said electroencephalographic data is accompanied by reviewing representations of simultaneously obtained portions of said electromyographic signal data and said electrooculographic signal data.

30. The method of claim 23 wherein said entering into a memory means of a selected third frequency value comprises estimating along said electroencephalographic frequency content representation an initial third frequency value, reviewing representations of portions of said electroencephalographic signal data from which those portions of said electroencephalographic frequency content representation having values near said initial third frequency value were obtained, determining where in said electroencephalographic signal data a transition region occurs between a portion of said electroencephalographic signal data consistent with each said type of sleep and another portion thereof consistent with waking, and entering in said memory means as said third frequency value that frequency value at which said transition region occurs.

31. The method of claim 30 wherein said reviewing of representations comprises displaying said representations of portions of said electroencephalographic signal data on said display means.

32. The method of claim 30 further comprising obtaining electrooculographic signal data from said subject, providing a representation of occurrences of selected eye movements indicated in said electrooculographic signal data, and presenting said eye movement occurrence representation on said display means, and wherein said reviewing of representations of portions of said electroencephalographic data is accompanied by reviewing representations of simultaneously obtained portions of said electromyographic signal data and said electrooculographic signal data.

33. The method of claim 23 wherein said entering into a memory means of a selected first signal strength value comprises estimating along said electromyographic signal strength content representation an initial first signal strength value, reviewing representations of portions of said electromyographic signal data from which those portions of said electromyographic signal strength representation having values near said initial first signal strength value were obtained, determining where in said electromyographic signal data a transition region occurs between a portion of said electromyographic signal data consistent with said fifth type of sleep and another portion thereof consistent with other types of sleep, and entering in said memory means as said selected first signal strength value that signal strength value at which said transition region occurs.

34. The method of claim 33 wherein said reviewing of representations comprises displaying said representations of portions of said electromyographic signal data on said display means.

35. The method of claim 33 further comprising obtaining electrooculographic signal data from said subject, providing a representation of occurrences of selected eye movements indicated in said electrooculographic signal data, and presenting said eye movement occurrence representation on said display means, and wherein said reviewing of representations of portions of said electromyographic data is accompanied by reviewing representations of simultaneously obtained portions of said electroencephalographic signal data and said electrooculographic signal data.

36. The method of claim 1 wherein said determining is preceded at least in part by finding occurrences of sleep spindles and K-complexes in said electroencephalographic signal data, and wherein said determining is further based on such occurrences.

37. The method of claim 36 wherein said finding of occurrences further comprises finding occurrences of movement arousals indicated jointly in said electromyographic signal data and said electroencephalographic signal data, and wherein said determining is further based on such occurrences.

38. The method of claim 37 wherein said determining further comprises determining any incidences of at least one of said types of sleep based both on giving effect to said occurrences and on giving no effect to said occurrences in such determination, followed by comparing incidences of that one said type of sleep as determined on each basis to one another.

39. The method of claim 36 wherein said determining further comprises determining any incidences of at least one of said types of sleep based both on giving effect to said occurrences and on giving no effect to said occurrences in such determination, followed by comparing incidences of that one said type of sleep as determined on each basis to one another.

40. A sleep stage monitoring system for providing determination of whether waking or any of a plurality of defined types of sleep, including first, second, third, fourth and fifth types of sleep, occur in data gathered from a subject, said system comprising:
 a signal acquiring means for acquiring an electroencephalographic signal, an electromyographic signal and an electrooculographic signal;
 an analog-to-digital converter means connected to said signal acquiring means for providing a first sequence of consecutive digitized samples of amplitude values of said electroencephalographic signal, a second sequence of consecutive digitized samples of amplitude values of said electromyographic signal, and a third sequence of consecutive digitized samples of amplitude values of said electrooculographic signal;
 a display and input means capable of providing displays of representations of said electroencephalographic signal, said electromyographic signal and said electrooculographic signal provided at inputs thereof, and capable of providing selected values at outputs thereof; and
 a signal processing means connected to said analog-to-digital converter means and to said inputs and outputs of said display and input means, and capable of providing a representation of frequency content of said electroencephalographic signal from said first sequence, of providing a representation of signal strength of said electromyographic signal from said second sequence, and of providing a representation of occurrences of selected eye movements indicated in said electrooculographic signal from said third sequence, and further capable of accepting selected frequency and signal strength values at outputs of said display and input means to provide a determination, based on said first sequence, said second sequence and said third sequence and on said frequency and signal strength values, whether waking or which of any of said types of sleep have been experienced by said subject as indicated in said electroencephalographic, said electromyographic and said electrooculographic signals.

41. The apparatus of claim 40 wherein said display and input means can display representations of said first sequence, said second sequence and said third sequence received at inputs thereof from said signal processing means.

* * * * *